United States Patent
Wang et al.

(10) Patent No.: US 9,977,140 B2
(45) Date of Patent: May 22, 2018

(54) MORE EFFICIENT METHOD AND APPARATUS FOR DETECTOR RESPONSE CORRECTION AND MATERIAL DECOMPOSITION OF PROJECTION DATA OBTAINED USING PHOTON-COUNTING DETECTORS

(71) Applicant: Toshiba Medical Systems Corporation, Otawara-shi (JP)

(72) Inventors: Xiaolan Wang, Buffalo Grove, IL (US); Yu Zou, Naperville, IL (US); Adam Petschke, Lake Bluff, IL (US); Zhou Yu, Palatine, IL (US); Chunguang Cao, Buffalo Grove, IL (US)

(73) Assignee: Toshiba Medical Systems Corporation, Otawara-shi (JP)

( * ) Notice: Subject to any disclaimer, the term of this patent is extended or adjusted under 35 U.S.C. 154(b) by 279 days.

(21) Appl. No.: 14/593,818

(22) Filed: Jan. 9, 2015

(65) Prior Publication Data

US 2016/0202364 A1 Jul. 14, 2016

(51) Int. Cl.
*G01T 7/00* (2006.01)
*A61B 6/03* (2006.01)
(Continued)

(52) U.S. Cl.
CPC .......... *G01T 7/005* (2013.01); *A61B 6/032* (2013.01); *A61B 6/4241* (2013.01); *A61B 6/482* (2013.01);
(Continued)

(58) Field of Classification Search
None
See application file for complete search history.

(56) References Cited

U.S. PATENT DOCUMENTS 8,194,961 B2 6/2012 Zou et al.
8,965,095 B2 2/2015 Zou et al.
(Continued)

OTHER PUBLICATIONS

Nuyts, Johan, et al. "Modelling the physics in the iterative reconstruction for transmission computed tomography." Physics in medicine and biology 58.12 (2013): R63.*

(Continued)

*Primary Examiner* — Vu Le
*Assistant Examiner* — Tracy Mangialaschi
(74) *Attorney, Agent, or Firm* — Oblon, McClelland, Maier & Neustadt, L.L.P.

(57) ABSTRACT

An apparatus and method of processing X-ray projection data including spectral computed tomography (CT) projection data. The spectral CT data is decomposed into material projection lengths using a material-decomposition method that includes an initial-estimate method to provide an initial projection-lengths estimate. The initial-estimate method can include first reconstructing an image using non-spectral CT data, and then subdividing the reconstructed image into materials according to the relative attenuation density of areas within the reconstructed image (e.g., high attenuation areas correspond to a high attenuation material such as bone). The projection length estimates of each material are then obtained by forward projecting the corresponding subdivision of the reconstructed image. Also, the initial estimate can be obtained/refined by selecting the projection lengths with smallest cost-function value from randomly chosen projection lengths within a sample space. The initial estimate can also be conditioned on the X-ray flux at the X-ray source.

19 Claims, 15 Drawing Sheets

(51) Int. Cl.
*A61B 6/00* (2006.01)
*G01T 1/18* (2006.01)
*G01N 23/20* (2018.01)
*G01N 23/04* (2018.01)
*G06T 11/00* (2006.01)

(52) U.S. Cl.
CPC ............ *A61B 6/5205* (2013.01); *A61B 6/585* (2013.01); *G01N 23/046* (2013.01); *G01N 23/20066* (2013.01); *G01T 1/18* (2013.01); *G06T 11/003* (2013.01); *G06T 11/005* (2013.01); *G06T 2207/10081* (2013.01); *G06T 2211/408* (2013.01); *G06T 2211/424* (2013.01)

(56) References Cited

U.S. PATENT DOCUMENTS

| | | | | |
|---|---|---|---|---|
| 2009/0080597 A1* | 3/2009 | Basu | ............ | A61B 5/4869 378/5 |
| 2013/0251097 A1 | 9/2013 | Zou et al. | | |
| 2013/0343624 A1* | 12/2013 | Thibault | ............... | G06T 11/006 382/131 |
| 2014/0355853 A1 | 12/2014 | Zou et al. | | |
| 2016/0128650 A1* | 5/2016 | Wang | .................... | A61B 6/482 378/5 |
| 2016/0217596 A1* | 7/2016 | Koehler | ................ | G06T 11/006 |

OTHER PUBLICATIONS

Beister, Marcel, Daniel Kolditz, and Willi A. Kalender. "Iterative reconstruction methods in X-ray CT." Physica medica 28.2 (2012): 94-108.*

Bornefalk, Hans, and Mats Persson. "Theoretical comparison of the iodine quantification accuracy of two spectral CT technologies." IEEE transactions on medical imaging 33.2 (2014): 556-565.*

Johnston, Samuel M., G. Allan Johnson, and Cristian T. Badea. "Temporal and spectral imaging with micro-CT." Medical physics 39.8 (2012): 4943-4958.*

* cited by examiner

True $c_1$
From spectral decomposition

Estimated $c_1$
From non-spectral 3rd-gen image

True Sinogram
Material 1 (water)

Estimate Sinogram
Material 1 (water)

True $c_2$
From spectral decomposition

Estimated $c_2$
From non-spectral 3$^{rd}$-gen image

True Sinogram
Material 2 (bone)

Estimate Sinogram
Material 2 (bone)

MORE EFFICIENT METHOD AND APPARATUS FOR DETECTOR RESPONSE CORRECTION AND MATERIAL DECOMPOSITION OF PROJECTION DATA OBTAINED USING PHOTON-COUNTING DETECTORS

BACKGROUND

Field

Embodiments described herein relate generally to spectral projection data, and more specifically to material decomposition of spectral projection data.

Description of the Related Art

Projection data can be used for many applications, including: computed tomography, radiography, mammography, and tomosynthesis. Projection data reveals the internal structure of an object by transmitting radiation through the object and detecting changes in the transmitted radiation relative to when the object is absent. In absorption imaging the projection data represents Radon transforms of the attenuation along the rays traced by the radiation. Computed tomography uses projection data at a series of projection angles to reconstruct an image of the internal structure of the object.

Computed tomography (CT) systems and methods are widely used, particularly for medical imaging and diagnosis. CT systems generally create images of one or more sectional slices through a subject's body. A radiation source, such as an X-ray source, irradiates the body from one side. A collimator, generally adjacent to the X-ray source, limits the angular extent of the X-ray beam, so that radiation impinging on the body is substantially confined to a planar region (i.e., an X-ray projection plane) defining a cross-sectional slice of the body. At least one detector (and generally many more than one detector) on the opposite side of the body receives radiation transmitted through the body in the projection plane. The attenuation of the radiation that has passed through the body is measured by processing electrical signals received from the detector. In some implementations a multi slice detector configuration is used, providing a volumetric projection of the body rather than planar projections.

Typically the X-ray source is mounted on a gantry that revolves about a long axis of the body. The detectors are likewise mounted on the gantry, opposite the X-ray source. A single cross-sectional image of the body is obtained by taking projective attenuation measurements at a series of gantry rotation angles, and processing the resultant data using a CT reconstruction algorithm. To obtain multiple cross-sectional images or a three-dimensional image, the X-ray sources and detectors must be translated relative to the body. The body is translated relative to the gantry, and a plurality of views may be acquired, each such view comprising attenuation measurements made at a different angular and/or axial position of the source. In some CT systems, the combination of translation of the body and the rotation of the gantry relative to the body is such that the X-ray source traverses a spiral or helical trajectory with respect to the body. The multiple views are then used to reconstruct a CT image showing the internal structure of the slice or of multiple such slices.

Because X-ray CT is the most common form of CT in medicine and various other contexts, the term computed tomography alone is often used to refer to X-ray CT, although other types exist (such as positron emission tomography and single-photon emission computed tomography). Other terms that also refer to X-ray CT are computed axial tomography (CAT scan) and computer-assisted tomography.

In one example of X-ray CT, X-ray slice data is generated using an X-ray source that rotates around the object; X-ray sensors are positioned on the opposite side of an image object from the X-ray source. Machines rotate the X-ray source and detectors around a stationary object. Following a complete rotation, the object is moved along its axis, and the next rotation started.

Newer machines permit continuous rotation with the object to be imaged slowly and smoothly slid through the X-ray ring. These are called helical or spiral CT machines. Systems with a very large number of detector rows along the axial direction perpendicular to the rotation axis are often termed cone beam CT, due to the shape of the X-ray beam.

Making projective measurements at a series of different projection angles through the body, a sinogram can be constructed from the projection data, with the spatial dimension of the detector array along one axis and the time/angle dimension along the other axis. The attenuation resulting from a particular volume within the body will trace out a sine wave oscillating along the spatial dimension of the sinogram, with the sine wave being centered on the axis of rotation for the CT system. Volumes of the body farther from the center of rotation correspond to sine waves with greater amplitudes. The phase of each sine wave in the sinogram corresponds to the relative angular positions around the rotation axis. Performing an inverse Radon transform (or an equivalent image reconstruction method) reconstructs an image from the projection data in the sinogram, where the reconstructed image corresponding to a cross-sectional slice of the body.

Conventionally, energy-integrating detectors have been used to measure CT projection data. Now, recent technological developments are making photon-counting detectors (PCDs) a feasible alternative to energy-integrating detectors. PCDs have many advantages including their capacity for performing spectral CT. To obtain the spectral nature of the transmitted X-ray data, the PCDs split the X-ray beam into its component energies or spectrum bins and count a number of photons in each of the bins.

Many clinical applications can benefit from spectral CT technology, which can provide improvement in material differentiation and beam hardening correction. Further, semiconductor-based PCDs are a promising candidate for spectral CT, which is capable of providing better spectral information compared with conventional spectral CT technology (e.g., dual-source, kVp-switching, etc.).

One advantage of spectral CT, and spectral X-ray imaging in general, is that materials having atoms with different atomic number Z also have different spectral profiles for attenuation. Thus, by measuring the attenuation at multiple X-ray energies, materials can be distinguished based on the spectral absorption profile of the constituent atoms (i.e., the effective Z of the material). Distinguishing materials in this manner enables a mapping from the spectral domain to the material domain. This mapping is conventionally referred to as material decomposition.

Material decomposition of spectral CT data is possible because the attenuation of X-rays in biological materials is dominated by two physical processes—photoelectric and Compton scattering. Thus, the attenuation coefficient as a function of energy can be approximated by the decomposition $$\mu(E,x,y) = \mu_{PE}(E,x,y) + \mu_C(E,x,y),$$

where $\mu_{PE}(E,x,y)$ is the photoelectric attenuation and $\mu_C(E,x,y)$ is the Compton attenuation. This attenuation coefficient can be rearranged instead into a decomposition of a material 1 (e.g., a high-Z material such as bone) and a material 2 (e.g., a low-Z material such as water) to become $$\mu(E,x,y) \approx \mu_1(E)c_1(x,y) + \mu_2(E)c_2(x,y),$$

where $c_{1,2}(x,y)$ is a spatial function describing the concentrations of material 1 and material 2 located at position (x,y).

While semiconductor-based PCDs provide unique advantages for spectral CT, they also create unique challenges. For example, without correcting for nonlinearities and spectral shifts in the detector response, images reconstructed from semiconductor-based PCDs can have poorer image quality. The detector response corrections are in response to pileup, ballistic deficit effects, polar effects, characteristic X-ray escape, and space-charge effects.

The combination of detector response correction and material decomposition creates a complex problem. There are iterative methods of accounting for the detector response and decomposing the projection data into material components referred to as projection lengths. However, in some cases the methods can iterate to an incorrect solution corresponding to a local rather than global minimum of the problem formulation. Therefore, beginning the iterative methods with a well-chosen initial estimate of the projection lengths is important to obtaining the optimal projection lengths.

BRIEF DESCRIPTION OF THE DRAWINGS

A more complete understanding of this disclosure is provided by reference to the following detailed description when considered in connection with the accompanying drawings, wherein.

DETAILED DESCRIPTION

Figure 1:
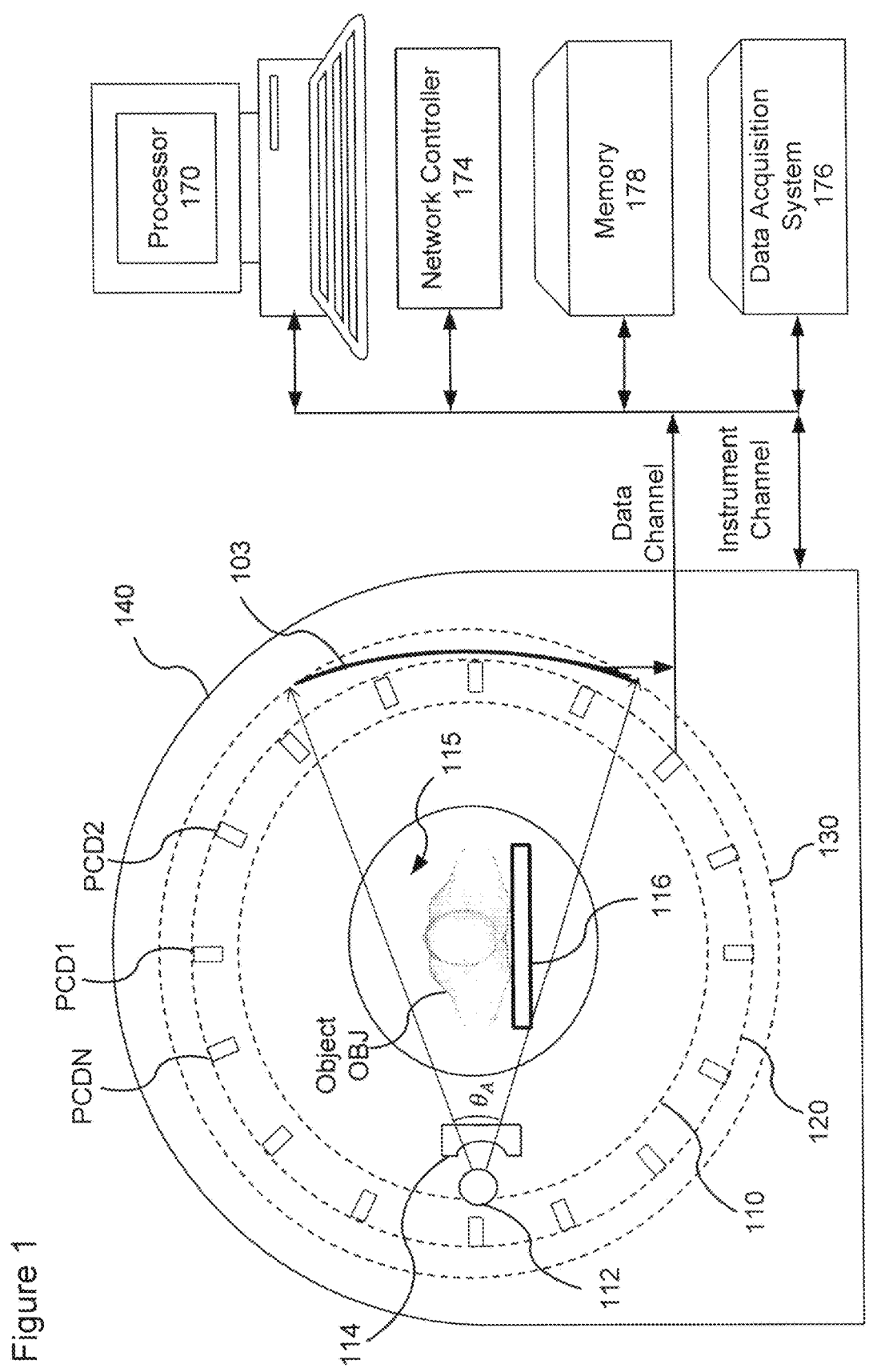
FIG. 1 shows a schematic of an implementation of a computed tomography scanner.

In spectral CT using photon-counting detectors (PCDs), image reconstruction is preceded by preprocessing steps including correcting for the detector response and material decomposition. In certain implementations, it can be beneficial to perform several of these preprocessing steps in combination.

For example, correcting for detector response and the material decomposition can be solved simultaneously by finding the projection lengths of materials 1 and 2 best satisfying the detector response equation, which is given by $$N_m = T \int dE (S_{Lin}(E) + S_{Nonlin}(E)) W_m(E)$$

wherein $N_m$ is the number of counts of the $m^{th}$ energy bin of a PCD, T is the integrating time, $W_m(E)$ is a window function representing the detection spectrum of the $m^{th}$ energy bin (i.e., $W_m(E)$ gives the probability-density that a detection event of energy E is recorded in the $m^{th}$ energy bin), $S_{Lin}(E)$ is the linear response of the PCD, which is given by $$S_{Lin}(E) = n e^{-n\tau} \int dE_0 R_0(E, E_0) S(E_0),$$

$S_{Nonlin}(E)$ is the nonlinear detector response of the PCD, which is given by $$S_{Nonlin}(E) = n^2 e^{-n\tau} \iint dE_0 dE_1 R_1(E, E_0, E_1)$$
$$S(E_0) S(E_1) + \ldots,$$

wherein the ellipsis denote higher order terms, which become more significant at higher flux densities, $R_0$ is the linear detector response function, $R_1$ is the first-order pileup detector response function, and $\tau$ is the dead time of the detector. The spectrum term S(E) in the integrand is the incident spectrum on the detector not including quantum efficiency, space charge effects, ballistic deficit, pileup, characteristic X-ray escape, and other effects coming after photo-absorption of the X-rays. This spectrum term is the given by $$S(E) = S_{air}(E) \exp[-\mu_1(E) L_1 - \mu_2(E) L_2]$$

wherein $\mu_1$ and $\mu_2$ are the attenuation coefficients of the basis materials for the material decomposition, and $L_1$ and $L_2$ are the respective projection lengths. The X-ray flux n for each detector is given by $$n = n_{air} \int dE_0 S_{air}(E_0) \exp[-\mu_1(E_0) L_1 - \mu_2(E_0) L_2],$$

wherein $n_{air} = A \cdot I_{ref}$ is the calculated flux based on a reference intensity measurement $I_{ref}$ of an X-ray source and A is a calibration factor. The factor $S_{air}$ represents the X-ray spectrum in the absence of an imaged object OBJ, i.e., $S_{air}$ identical to S when the imaged object OBJ is replaced by air). Similarly, the factor $n_{air}$ represents the X-ray flux at the detector in the absence of an imaged object OBJ. For each projection measurement, the reference intensity $I_{ref}$ is measured by the reference detector near the X-ray source before the imaged object OBJ. The reference intensity measurement is performed using a non-spectral reference detector (e.g., an energy-integrating detector).

There are at least two methods for solving the above detector-response equations and obtaining the projection lengths $L_1$ and $L_2$. In one implementation, an iterative detector-model based method uses estimates of the projection lengths to correct detector signals, and then using the corrected signals to update estimates of the projection lengths in an iterative fashion. The iterative detector-model based method assumes a model of the detector response to calculate a first estimate of the projection lengths $L_1$ and $L_2$. Then using this first estimate, material decomposition is performed using, e.g., a two energy material decomposition to calculate a second estimate of the projection lengths $L_1$ and $L_2$. The second estimate is then used to obtain a third estimate using the assumed model of the detector response, and so forth until the estimates of the projection lengths $L_1$ and $L_2$ converge.

Another method for solving the above detector-response equations and obtaining the projection lengths $L_1$ and $L_2$ uses a cost-function. The cost-function method solves for the projection lengths by finding the global optimum of a cost-function representing the difference between the measured counts $N'_m$ and the calculated counts $N_m$ using the detector response equation. Several different cost functions $\varphi(L_1, L_2)$ are possible. In one implementation, the cost function is the least squares of the difference between the measured counts $N'_m$ and the calculated counts $N_m$, i.e., $$\varphi(L_1, L_2) = \Sigma(N'_m - N_m)^2.$$

In one implementation, the cost function is the weighted least squares of the difference between the measured counts $N'_m$ and calculated counts $N_m$, i.e., $$\varphi(L_1, L_2) = \sum \frac{(N'_m - N_m)^2}{\sigma_m^2},$$

where $\sigma_m$ is the standard deviation of $N'_m$.

In one implementation, the cost function is the Poisson likelihood function, i.e., $$\varphi(L_1, L_2) = \Sigma[N'_m \log(N_m) - N_m].$$

Both of these solutions to the projection-lengths-detector-response problem rely on iterative methods starting from an initial estimate of the projection lengths. These iterative methods are most effective when beginning with a well-chosen initial estimate of the projection lengths. Methods are described herein for choosing the initial projection length estimate.

In one implementation of the initial-estimate method, an attenuation image is reconstructed using projection data from non-spectral energy-integrating detectors. This reconstructed image is then subdivided into regions corresponding respectively to a first and second material component. Projection lengths for the first material component are obtained by performing forward projections on the regions of the reconstructed image corresponding to the first material, and projection lengths for the second material component are obtained by performing forward projections on the regions of the reconstructed image corresponding to the second material. This implementation is especially applicable for hybrid CT systems having both energy-integrating detectors and PCDs, but is also applicable when non-spectral CT data can be obtained by other means, e.g., by summing over the spectral dimension of spectral CT data.

In another implementation of the initial-estimate method, the initial estimate of the projection lengths is obtained by calculating the cost function for a randomly chosen set of projection lengths within a sample space. The initial estimate is then selected from among these randomly chosen projection lengths by selecting the projection lengths corresponding to the smallest value of a cost function. The cost-function represents the difference between the measured counts $N'_m$ and the calculated counts $N_m$ using the detector response equation. This implementation is applicable to any CT system capable of acquiring spectral CT data.

In yet another implementation of the initial-estimate method, the choice of the initial estimate is conditioned on the incident flux density $n_{air}$ in order to preferentially select an initial estimate corresponding to a steeper gradient of the cost function and/or an initial estimate that is more likely to lead to a solution that is a global minimum of a cost function. By choosing an initial estimate corresponding to a steeper gradient, iterative methods based on gradient descent are more likely to converge quickly.

In one implementation of the cost function, for low-flux densities, the gradient of cost function is generally steeper for projection lengths that are less than the optimal projection lengths; whereas, for high-flux densities the gradient of cost function is generally steeper for projection lengths that are greater than the optimal projection lengths. Further, for high-flux densities local minima are more likely to be avoided by an initial estimate of the projection lengths that is greater than the optimal projection lengths.

Each of the above implementations can be combined in various permutations.

Referring now to the drawings, wherein like reference numerals designate identical or corresponding parts throughout the several views, FIG. 1 shows a schematic view of a hybrid CT scanner system having energy-integrating detectors arranged in a third-generation geometry and photon-counting detectors (PCDs) arranged in a fourth-generation geometry. The CT scanner is arranged in a coupled ring topology with the X-ray source 112 inside the ring of PCDs and the X-ray detector unit 103 is outside the ring of PCDs, as discussed in U.S. patent application Ser. No. 13/426,903, incorporated herein by reference in its entirety.

Illustrated in FIG. 1 is an implementation for placing the PCDs in a predetermined fourth-generation geometry in combination with a detector unit 103 in a predetermined third-generation geometry in a CT scanner system. The diagram illustrates relative positions among an object OBJ to be scanned resting on a table 116, an X-ray source 112, a collimator/filter 114, an X-ray detector 103, and photon-counting detectors PCD1 through PCDN. The PCDs have a front surface, oriented towards the object OBJ and a back surface oriented away from the object OBJ. X-rays traveling through the object OBJ are either detected by the PCDs (at the front surface) or pass through the spaces between the sparsely arranged PCDs and are detected by the tightly packed energy-integrating detectors in the X-ray detector 103.

Also shown in FIG. 1 is circuitry and hardware for acquiring, storing, processing, and distributing X-ray projection data. The circuitry and hardware include: a processor 170, a network controller 174, a memory 178, and a data acquisition system 176.

In one implementation, the X-ray source 112 and the collimator/filter 114 are fixedly connected to a rotational component 110 that is rotatably connected to a gantry 140. The X-ray detector 103 is similarly fixedly connected to a rotational component 130 that is rotatably connected to the gantry 140. While, the PCDs are fixedly connected to a circular component 120 that is fixedly connected to the gantry 140. The gantry 140 houses many pieces of the CT scanner.

The gantry of the CT scanner also includes an open aperture 115 enabling the object OBJ that is arranged on a table 116 positioned in a projection plane of the X-rays traveling from the X-ray source to the PCDs and detector unit 103. The "projection plane" is a volume wherein X-rays pass from the X-ray source 112 to the detectors including the PCDs and the detector unit 103. The "object space" is the intersection of the projection plane and the open aperture 115 of the gantry. The "image space" includes the union of projection planes corresponding to all projection angles of the X-ray source 112 as the X-ray source 112 rotates around the aperture of the gantry.

A scan is performed when an object OBJ occupies the object space and the X-ray source is rotated through a series of projection angles with the CT scanner acquiring projection data of the X-ray transmission/attenuation through the object OBJ at each projection angle.

In general, the photon-counting detectors PCD1 through PCDN each output a photon count for each of a predetermined number of energy bins. In addition to the photon-counting detectors PCD1 through PCDN arranged in the fourth-generation geometry, the implementation shown in FIG. 1 includes a detector unit 103 having energy-integrating detectors arranged in a conventional third-generation geometry. The detector elements in the detector unit 103 can be more densely placed along the detector unit surface than the photon-counting detectors.

In one implementation, the photon-counting detectors are sparsely placed around the object OBJ in a predetermined geometry such as a circle. For example, the photon-counting detectors PCD1 through PCDN are fixedly placed on a predetermined second circular component 120 in a gantry. In one implementation, the photon-counting detectors PCD1 through PCDN are fixedly placed on the circular component 120 at predetermined equidistant positions. In an alternative implementation, the photon-counting detectors PCD1 through PCDN are fixedly placed on the circular component 120 at predetermined non-equidistant positions. The circular component 120 remains stationary with respect to the object OBJ and does not rotate during the data acquisition.

Both the X-ray source 112, collimator 114 (e.g., a bow tie filter), and the detector unit 103 rotate around the object OBJ while the photon-counting detectors PCD1 through PCDN are stationary with respect to the object OBJ. In one implementation, the X-ray source 112 projects X-ray radiation with a predetermined source fan beam angle $\theta_A$ towards the object OBJ while the X-ray source 112 rotates around the object OBJ outside the sparsely placed photon-counting detectors PCD1 through PCDN. Furthermore, the detector unit 103 is mounted at a diametrically opposed position from the X-ray source 112 across the object OBJ and rotates outside the stationary circular component 120, on which the photon-counting detectors PCD1 through PCDN are fixed in a predetermined sparse arrangement.

In one implementation, the X-ray source 112 optionally travels a helical path relative to the object OBJ, wherein the table 116 moves the object OBJ linearly in a predetermined direction perpendicular to the rotational plane of the rotating portion 110 as the rotating portion 110 rotates the X-ray source 112 and detector unit 103 in the rotational plane.

The motion of the rotating portion 110 around the object OBJ is controlled by a motion control system. The motion control system can be integrated with a data acquisition system or can be separate providing one way information regarding the angular position of the rotating portion 110 and the linear position of the table 116. The motion control system can include position encoders and feedback to control the position of the rotating portion 110 and the table 116. The motion control system can be an open loop system, a closed loop system, or a combination of an open loop system and a closed loop system. The motion control system can use linear and rotary encoders to provide feedback related to the position of the rotating portion 110 and the position of the table 116. The motion control system can use actuators to drive the motion of the rotating portion 110 and the motion of the table 116. These positioners and actuators can include: stepper motors, DC motors, worm drives, belt drives, and other actuators known in the art.

The CT scanner also includes a data channel that routes projection measurement results from the photon counting detectors and the detector unit 103 to a data acquisition system 176, a processor 170, memory 178, network controller 174. The data acquisition system 176 controls the acquisition, digitization, and routing of projection data from the detectors. The data acquisition system 176 also includes radiography control circuitry to control the rotation of the annular rotating frames 110 and 130. In one implementation data acquisition system 176 will also control the movement of the bed 116, the operation of the X-ray source 112, and the operation of the X-ray detectors 103. The data acquisition system 176 can be a centralized system or alternatively it can be a distributed system. In an implementation, the data acquisition system 176 is integrated with the processor 170. The processor 170 performs functions including reconstructing images from the projection data, pre-reconstruction processing of the projection data, and post-reconstruction processing of the image data.

The pre-reconstruction processing of the projection data can include a calibration, correcting for detector nonlinearities, polar effects, noise balancing, and material decomposition.

Post-reconstruction processing can include filtering and smoothing the image, volume rendering processing, and image difference processing as needed. The image reconstruction process can be performed using filtered back projection, iterative image reconstruction methods, or stochastic image reconstruction methods. Both the processor 170 and the data acquisition system 176 can make use of the memory 176 to store, e.g., projection data, reconstructed images, calibration data and parameters, and computer programs.

The processor 170 can include a CPU that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the memory may be non-volatile, such as ROM, EPROM, EEPROM or FLASH memory. The memory can also be volatile, such as static or dynamic RAM, and a processor, such as a microcontroller or microprocessor, may be provided to manage the electronic memory as well as the interaction between the FPGA or CPLD and the memory.

Alternatively, the CPU in the reconstruction processor may execute a computer program including a set of computer-readable instructions that perform the functions described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xenon processor from Intel of America or an Opteron processor from AMD of America and an operating system, such as Microsoft VISTA, UNIX, Solaris, LINUX, Apple, MAC-OS and other operating systems known to those skilled in the art. Further, CPU can be implemented as multiple processors cooperatively working in parallel to perform the instructions.

In one implementation, the reconstructed images can be displayed on a display. The display can be an LCD display, CRT display, plasma display, OLED, LED or any other display known in the art.

The memory 178 can be a hard disk drive, CD-ROM drive, DVD drive, FLASH drive, RAM, ROM or any other electronic storage known in the art.

The network controller 174, such as an Intel Ethernet PRO network interface card from Intel Corporation of America, can interface between the various parts of the CT scanner. Additionally, the network controller 174 can also interface with an external network. As can be appreciated, the external network can be a public network, such as the Internet, or a private network such as an LAN or WAN network, or any combination thereof and can also include PSTN or ISDN sub-networks. The external network can also be wired, such as an Ethernet network, or can be wireless such as a cellular network including EDGE, 3G and 4G wireless cellular systems. The wireless network can also be WiFi, Bluetooth, or any other wireless form of communication that is known.

In one implementation, the X-ray source 112 is optionally a single energy source. In another implementation, the X-ray source 112 is configured to perform a kV-switching function for emitting X-ray radiation at a predetermined high-level energy and at a predetermined low-level energy. In still another alternative embodiment, the X-ray source 112 is a single source emitting a broad spectrum of X-ray energies. In still another embodiment, the X-ray source 112 includes multiple X-ray emitters with each emitter being spatially and spectrally distinct.

The detector unit 103 can use energy-integrating detectors such as scintillation elements with photo-multiplier tubes or avalanche photo-diodes to detect the resultant scintillation photons from scintillation events resulting from the X-ray radiation interacting with the scintillator elements. The scintillator elements can be crystalline (e.g., NaI(Tl), CsI (Tl), CsI(Na), CsI(pure), CsF, KI(Tl), LiI(Eu), BaF$_2$, CaF$_2$ (Eu), ZnS(Ag), CaWO$_4$, CdWO$_4$, YAG(Ce), Y$_3$Al$_5$O$_{12}$(Ce), GSO, LSO, LaCl$_3$(Ce), LaBr$_3$(Ce), LYSO, BGO, LaCl$_3$ (Ce), LaBr$_3$(Ce), C$_{14}$H$_{10}$, C$_{14}$H$_{12}$, and C$_{10}$H$_8$), an organic liquid (e.g., an organic solvent with a fluor such as p-terphenyl (C$_{18}$H$_{14}$), PBD (C$_{20}$H$_{14}$N$_2$O), butyl PBD (C$_{24}$H$_{22}$N$_2$O), or PPO (C$_{15}$H$_{11}$NO)), a plastic (e.g., a flour suspended in a solid polymer matrix), or other know scintillator.

The PCDs can use a direct X-ray radiation detectors based on semiconductors, such as cadmium telluride (CdTe), cadmium zinc telluride (CZT), silicon (Si), mercuric iodide (HgI$_2$), and gallium arsenide (GaAs). Semiconductor based direct X-ray detectors generally have much faster time response than indirect detectors, such as scintillator detectors. The fast time response of direct detectors enables them to resolve individual X-ray detection events. However, at the high X-ray fluxes typical in clinical X-ray applications some pile-up of detection events will occur. The energy of a detected X-ray is proportional to the signal generated by the direct detector, and the detection events can be organized into energy bins yielding spectrally resolved X-ray data for spectral CT.

Having obtained spectral CT projection data, the spectral CT imaging system using the processor 170 will perform a material decomposition on the spectral CT projection data to obtain projection lengths $L_1$ and $L_2$ corresponding respectively to a first and second material (e.g., a high-Z material such as bone and a low-Z material such as water). Performing this material decomposition is complicated by nonlinearities of the PCDs' response, by characteristic X-ray escape, and by beam hardening due to variations of the absorption coefficient as a function of X-ray energy.

Figure 3:
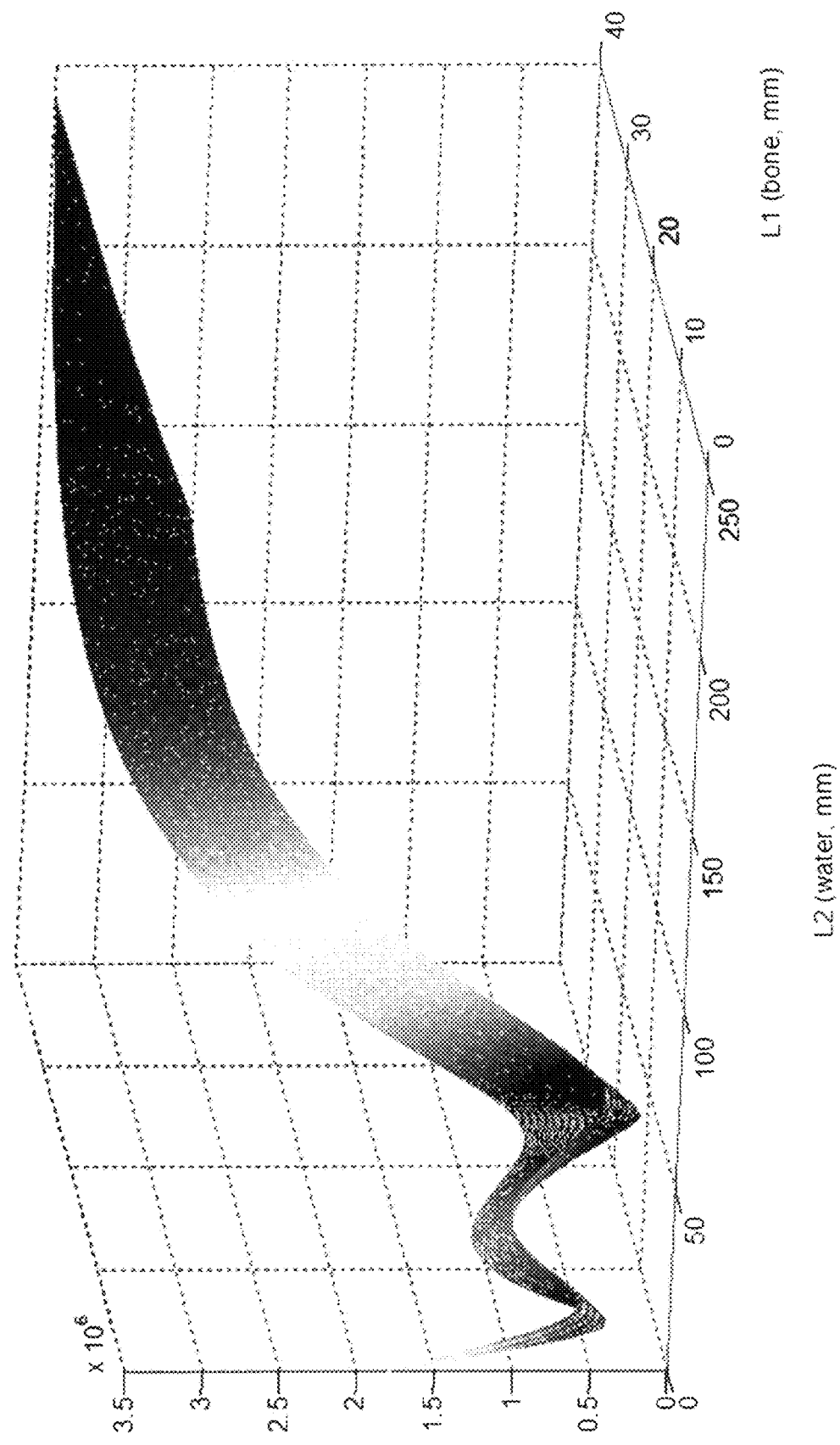
FIG. 3 shows a plot of a cost function (vertical axis) as a function of a first projection length of a first material (bone) and a second projection length of a second material (water)

As a result of these complications, there may be multiple sets of projection lengths, each appearing to be solutions of the material decomposition problem (e.g., many local minima of the projection-length cost function shown in FIG. 3). However, only one set of projection lengths is the actual solution of the material decomposition problem (e.g., the global minimum of the projection-length cost function shown in FIG. 3). While there is no analytical solution to the coupling of the material-decomposition problem and the detector-response problem, iterative methods can obtain solutions to these coupled problems using a gradient descent or related search method when starting from a well-chosen initial estimate of the projection lengths $L_1$ and $L_2$.

Figure 2:
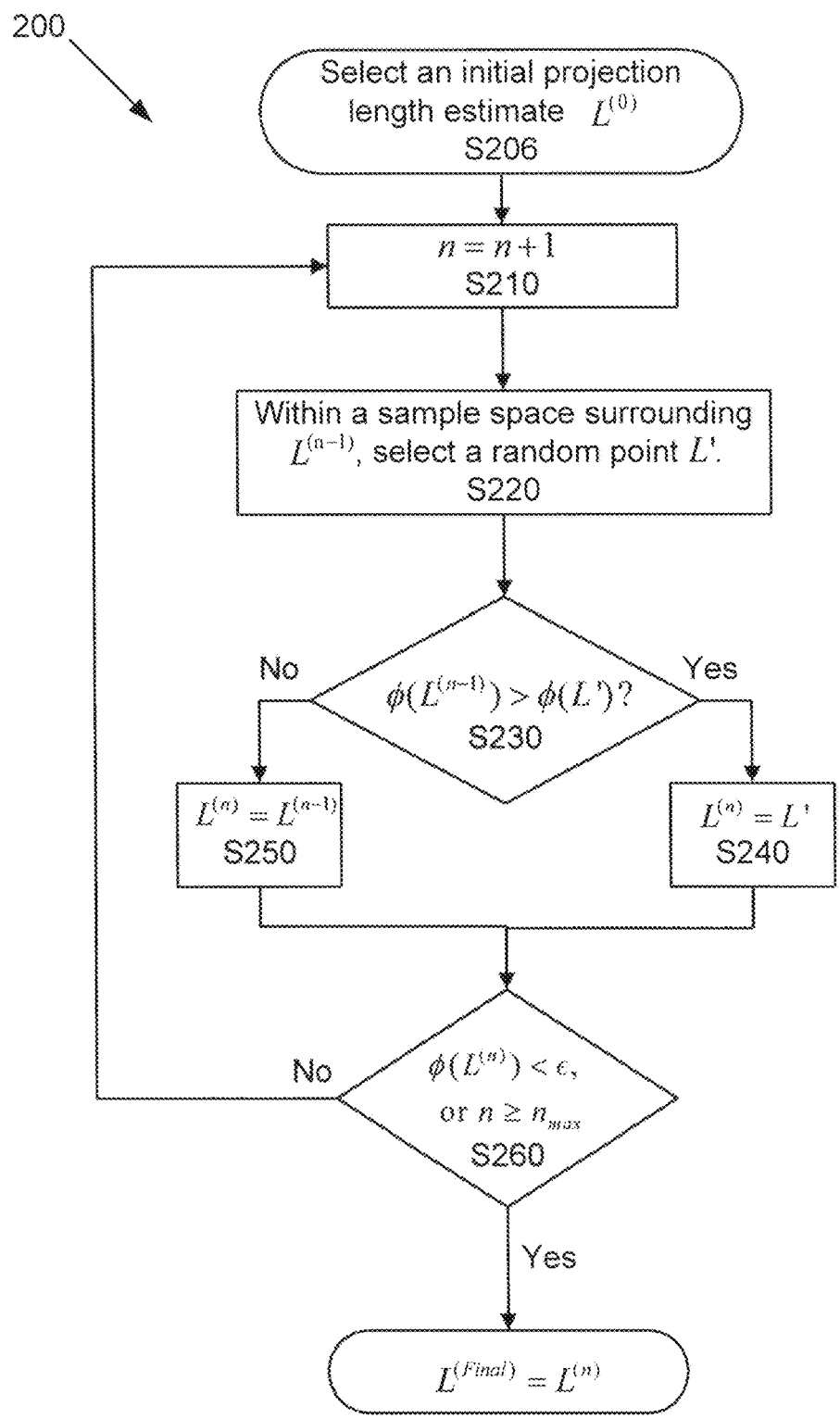
FIG. 2 shows a flow diagram of an implementation of an iterative cost-function method for finding projection lengths.
Figure 4:
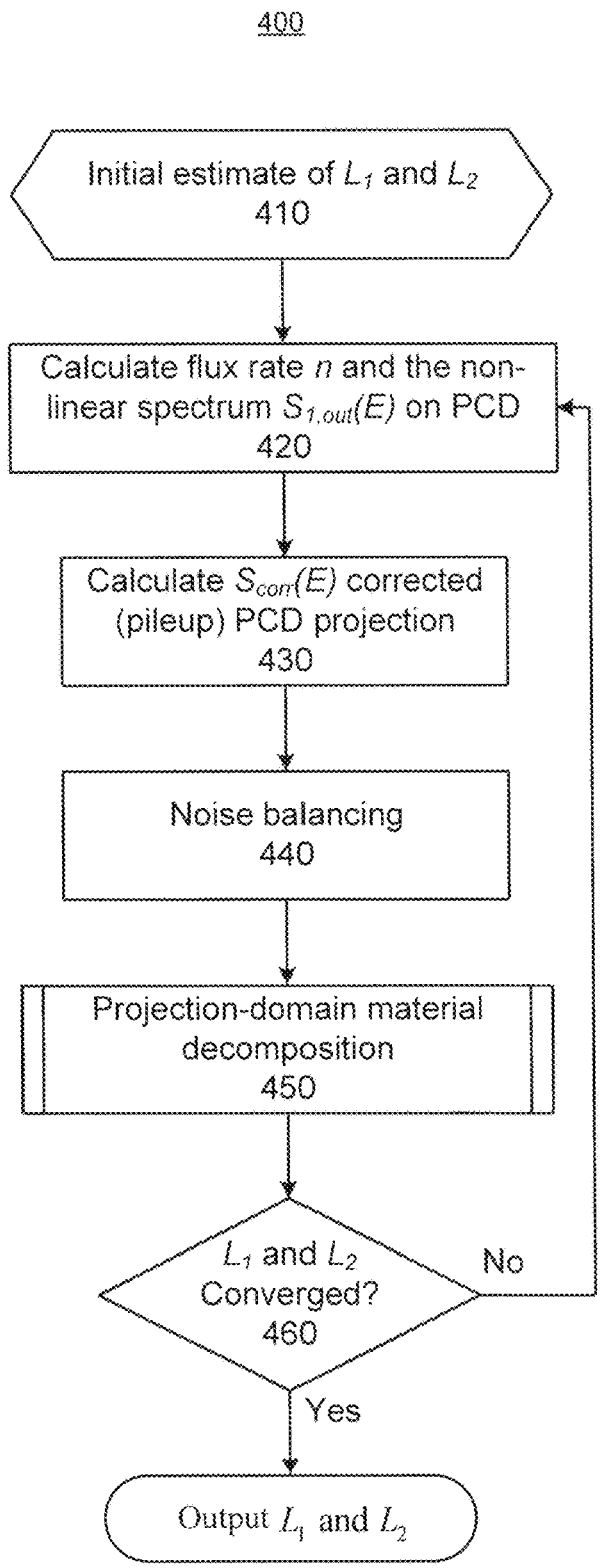
FIG. 4 shows a flow diagram of an implementation of an iterative method for finding projection lengths, splitting the steps of detector-response correction and material decomposition.

FIGS. 2 and 4 show two iterative methods of solving the material decomposition problem. Both depend on a well-chosen initial estimate of the projection lengths. The method shown in FIG. 2 uses a cost-function approach. The method shown in FIG. 4 uses an iterative approach wherein the material decomposition and the detector response correction are performed in separate steps.

The detector response will generally be different for each PCD, as well as for each projection angle, due to at least the polar effect. Therefore, the calibration coefficients will generally be obtained by calibration measurements performed at each projection angle of an imaging scan.

FIG. 2 shows a method 200 of iteratively solving for the optimal projection lengths $L^{Final}=(L_1, L_2)$ by minimizing the cost function $\varphi(L_1, L_2)$. This cost function combines the measured projection data $N'_m$ with corresponding calculated values $N_m$ obtained from the detector model discussed previously.

Several different cost functions $\varphi(L_1, L_2)$ are possible. In one implementation, the cost function is the least squares of the difference between the measured counts $N'_m$ and the calculated counts $N_m$, i.e., $$\varphi(L_1, L_2) = \sum_m (N'_m - N_m)^2.$$

In one implementation, the cost function is the weighted least squares of the difference between the measured counts $N'_m$ and calculated counts $N_m$, i.e., $$\varphi(L_1, L_2) = \sum_m \frac{(N'_m - N_m)^2}{\sigma_m^2},$$

where $\sigma_m$ is a measure of the measurement uncertainty of the $m^{th}$ energy bin of detector.

In one implementation, the cost function is the Poisson likelihood function, i.e., $$\varphi(L_1, L_2) = \sum_m [N'_m \log(N_m) - N_m].$$

In FIG. 2, the process 200 starts when a random value is selected as the initial guess for $L^{(0)} = (L_1^{(0)}, L_2^{(0)})$. Next, at step S210 the loop variable n is incremented.

Following step S210, the process 200 proceeds to step S220, wherein a new sample point L' is randomly selected from the sample space surrounding the current set of projection lengths $L^{(n-1)} = (L_1^{(n-1)}, L_2^{(n-1)})$.

Proceeding to step S230, the process 200 inquiries as to which value of the cost function $\varphi(L^{(n-1)})$ or $\varphi(L')$ is smaller. In steps S240 and S250, the argument corresponding to the smaller value of the cost function is assigned as the next set of projection lengths $L^{(n)} = (L_1^{(n)}, L_2^{(n)})$ for the next loop iteration.

Step S260 of process 200 evaluates whether the loop stopping criteria is satisfied. Although different stopping criteria can used, FIG. 2 shows an implementation wherein the loop stops when either a maximum number of loop iterations $n_{max}$ has been reached or the cost function falls below a predetermined threshold E. If the stopping criteria are satisfied, the process 200 exits the loop at S260 and reports the current projection length $L^{(n)} = (L_1^{(m)}, L_2^{(m)})$ as the final projection length. Otherwise, the loop continues by proceeding from step S260 back to step S210.

FIG. 3 shows an example of a least-squares cost function having a local minimum and a global minimum. A method that attempts to find the global minimum of the cost function should ensure that the projection lengths obtained from an iterative search correspond to true global minimum rather than a purely local minimum of the cost function. Generally, there is no algorithm that guarantees convergence for all cases due to the nonlinearities associated with pileup and beam hardening induced by polychromatic X-ray beams. However, using well-chosen initial values for the projection lengths significantly increases the likelihood that the obtained projection lengths correspond to the global minimum.

FIG. 4 shows a method 400 of iteratively solving for the optimal projection lengths $L^{Final} = (L_1, L_2)$. Method 400 differs from method 200 in that the material decomposition in method 400 occurs in a different step (i.e., process 450) from the detector response correction step (i.e., 430), whereas in method 200, both the material decomposition and detector response correction are implicit in the cost function and are therefore accounted for in a single step.

As shown in FIG. 4, method 400 begins when an initial estimate of the projection lengths $L_1$ and $L_2$ are input into the first step 420 of an iterative loop. After the first iteration of the large loop including steps 420 through 460, the projection lengths $L_1$ and $L_2$ are feedback from material decomposition in process 450 to the first step 420 of the large iterative loop. In contrast to subsequent loop iterations using projection lengths calculated by the material decomposition in process 450, the first iteration uses the initial estimate of the projection lengths from step 410.

Receiving the projection length estimates, the large loop begins at step 420 by calculating the X-ray flux rate $$n = n_{air} \int dE_0 S_{air}(E_0) \exp[-\mu_1(E_0)L_1 - \mu_2(E_0)L_2],$$

and the nonlinear spectrum term $S_{Nonlin.}(E)$ discussed previously. In the implementation shown in FIG. 4, the nonlinear spectrum includes only the first order pileup, which is given by $$S_{1,out} = \iint dE_0 dE_1 R_1(E, E_0, E_1) S_{in}(E_0) S_{in}(E_1),$$

wherein $$S_{in}(E) = S_{air}(E) \exp[-\mu_1(E)L_1 - \mu_2(E)L_2].$$

Next at step 830 of method 800, the corrected detector spectrum is calculated correcting for pileup according to $$S_{Corr.}(E) = S_{Raw}(E) - S_{Nonlin.}(E),$$

wherein $S_{Raw}(E)$ is the raw measured spectrum before detector response corrections. The corrected energy count is given by $$N_m^{Corr.} = T \int dE W_m(E) S_{Corr.}(E),$$

where T is the integration time.

In one implementation, the corrected count of the $m^{th}$ energy bin of the PCD is given by $$N_m^{Corr.} = N_m^{Raw} - N_m^{Nonlin.}$$

where $N_m^{Corr.}$ is the corrected count value of the $m^{th}$ energy bin of the PCD, $N_m^{Raw}$ is the raw count value recorded from the detector, and $N_m^{Nonlin.}$ is the calculated count from the nonlinear detector response. The nonlinear count value $N_m^{Nonlin.}$ is calculated according to $$N_m^{Nonlin.} = T \int dE w_m(E) S_{Nonlin.}(E).$$

In some implementations, the nonlinear spectrum correction includes only the first order pileup, while in other implementations, the nonlinear spectrum correction includes higher-order pileup terms.

The method 400 then proceeds to step 440. In step 440, noise balancing is performed by dividing the detector counts into high- and low-energy components in preparation for material decomposition. The noise-balancing process of apportioning the counts into high- and low-energy components is described in U.S. patent application Ser. No. 13/906,110, incorporated herein by reference in its entirety. Noise balancing enables the delineation between the high spectrum and the low spectrum to be different for different detectors in order to prevent the case where the signal-to-noise ratio for either the high- or low-energy components counts are significantly lower than the other energy component (i.e., the signal-to-noise ratios of the high- and low-energy components become unbalanced) and degrades the image quality of the reconstructed image. Noise balancing can be different for each PCD.

The noise balancing in step 440 results in partitioning the counts from the energy bins into high- and low-energy components according to $$N_H = \sum_m a_m^{(H)} N_m^{Corr},$$

and $$N_L = \sum_m a_m^{(L)} N_m^{Corr},$$

where $\sum_m a_m^{(H)}=1$, $\sum_m a_m^{(L)}=1$, and the values $a_m^{(H)}$ and $a_m^{(L)}$ are determined by the noise-balancing process.

Next method 400 proceeds to process 450. In process 450 the material decomposition is performed, wherein new values for the projection lengths $L_1$ and $L_2$ are calculated.

Finally, at step 460, an inquiry is made into whether the stopping criteria have been satisfied. The stopping criteria can depend on convergence of the projection lengths $L_1$ and $L_2$, and whether the maximum number of loop iterations have been reached.

Figure 5:
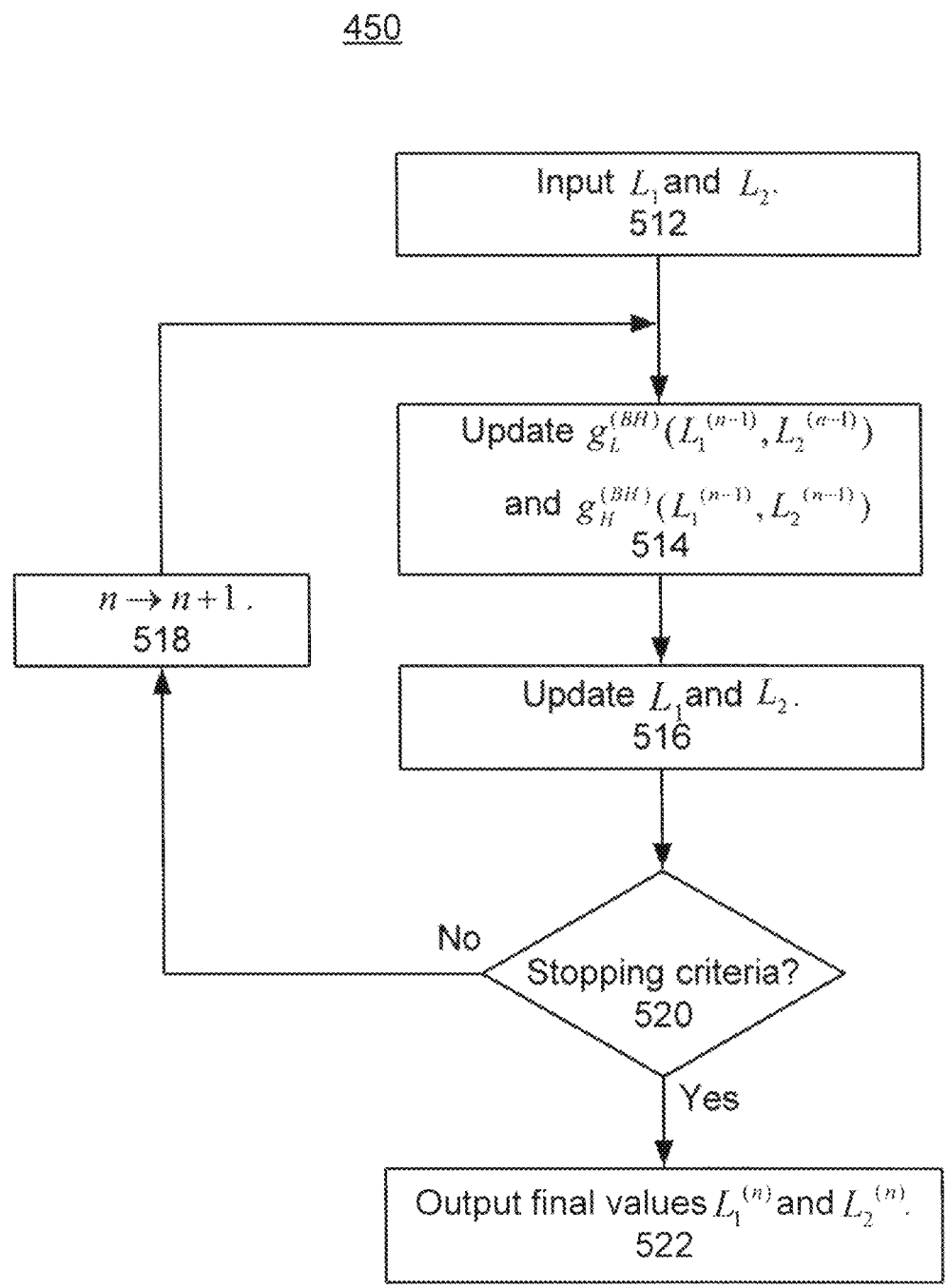
FIG. 5 shows a flow diagram of an implementation of an iterative material-decomposition method.

Also, the material decomposition process 450 can be an iterative process—as shown in FIG. 5—with its own stopping criteria. This iterative process is often referred to as the small loop, in contrast to the large loop including steps 420 through 460. The small loop stopping criteria of the process 450 can depend on the current iteration number of the large loop. For example, in one implementation, the stopping criteria of the small loop can have a more relaxed convergence threshold and a decreased maximum number of iterations when the large-loop iteration variable is small, preventing the small loop from over optimizing while the estimated projection lengths are still changing significantly with each iteration of the large loop.

In one implementation, process 450 is performed according to the method shown in FIG. 5, as discussed in U.S. Pat. No. 8,194,961, incorporated herein by reference in its entirety. Similar to the detector counts for the high- and low-energy components, the high and low spectra can be given by $$S_H(E) = \sum_m a_m^{(H)} S_{air}(E),$$

and $$S_L(E) = \sum_m a_m^{(L)} S_{air}(E),$$

where $S_H(E)$ and $S_L(E)$ are respectively the detected high- and low-energy spectra in the absence of the object OBJ (i.e., the object OBJ is air), and where $S_H(E)$ and $S_L(E)$ have been normalized such that $$\int dE\, S_H(E) = \int dE\, S_L(E) = 1.$$

By taking the natural logarithm of the detector counts, the log-projection data can be obtained as $$g_H(l) = -\ln(N_H/N_H^{air}) \text{ and}$$

$$g_L(l) = -\ln(N_L/N_L^{air}).$$

In one implementation, as shown in FIG. 5, $L_1$ and $L_2$ are found using perturbation theory by treating the variations around the mean of the attenuation coefficients $\mu_1(E)$ and $\mu_2(E)$ as perturbations. First, the mean attenuation for the high- and low-energy spectra are given by $$\bar{\mu}_{1,2}^{H,L} = \int S_{H,L}(E)\mu_{1,2}(E)dE,$$

and the variations around the mean are given by $$\Delta\mu_{1,2}^{H,L}(E) = \mu_{1,2}(E) - \bar{\mu}_{1,2}^{H,L}.$$

Thus, the log-projection data can be expressed as $$g_H(l) = -\ln\int S_H(E)\exp[-\bar{\mu}_1^H L_1(l) - \Delta\mu_1^H(E)L_1(l) - \bar{\mu}_2^H L_2(l) - \Delta\mu_2^H(E)L_2(l)]dE$$

$$g_L(l) = -\ln\int S_L(E)\exp[-\bar{\mu}_1^L L_1(l) - \Delta\mu_1^L(E)L_1(l) - \bar{\mu}_2^L L_2(l) - \Delta\mu_2^L(E)L_2(l)]dE.$$

Simplifying these expressions, the log-projection data can be written as $$g_H(l) = \bar{\mu}_1^H L_1(l) + \bar{\mu}_2^H L_2(l) - g_H^{(BH)}(L_1(l), L_2(l))$$

$$g_L(l) = \bar{\mu}_1^L L_1(l) + \bar{\mu}_2^L L_2(l) - g_L^{(BH)}(L_1(l), L_2(l))$$

where $$g_{H,L}^{(BH)}(L_1(l), L_2(l)) = \ln\int S_{H,L}(E)\exp[-L_1(l)\Delta\mu_1^{H,L}(E) - L_2(l)\Delta\mu_2^{H,L}(E)]dE$$

is the beam-hardening perturbation.

The first step 512 of process 450 initializes the iteration variable to n=0 and also initializes the values of the projection lengths $L_1$ and $L_2$. In one implementation, the initial values of the projection lengths are the same values used for the detector response correction calculation in step 420. In another implementation, the initial values of the projection lengths are the zeroth-order perturbation values calculated by solving the matrix equation $$\begin{pmatrix} g_H \\ g_L \end{pmatrix} = \begin{pmatrix} \bar{\mu}_1^H & \bar{\mu}_2^H \\ \bar{\mu}_1^L & \bar{\mu}_2^L \end{pmatrix} \begin{pmatrix} L_1 \\ L_2 \end{pmatrix}$$

to obtain $$\begin{pmatrix} L_1 \\ L_2 \end{pmatrix} = D^{-1} \begin{pmatrix} \bar{\mu}_2^L & -\bar{\mu}_2^H \\ -\bar{\mu}_1^L & \bar{\mu}_1^H \end{pmatrix} \begin{pmatrix} g_H \\ g_L \end{pmatrix}$$

where D is the determinant $D = \bar{\mu}_1^H \bar{\mu}_2^L - \bar{\mu}_1^L \bar{\mu}_2^H$.

The second step 514 of process 450 and the first step in the iterative loop is updating the beam-hardening perturbation values using the $n^{th}$ order perturbation in the equation $$g_{H,L}^{(BH)}(L_1(l), L_2(l)) = \ln\int S_{H,L}(E)\exp[-L_1(l)\Delta\mu_1^{H,L}(E) - L_2(l)\Delta\mu_2^{H,L}(E)]dE.$$

The third step 516 of process 450 is to update the values of $L_1$ and $L_2$ by solving for the $n+1^{th}$ perturbation by solving the matrix equation $$\begin{pmatrix} g_H + g_H^{(BH)}(L_1, L_2) \\ g_L + g_L^{(BH)}(L_1, L_2) \end{pmatrix} = \begin{pmatrix} \bar{\mu}_1^H & \bar{\mu}_2^H \\ \bar{\mu}_1^L & \bar{\mu}_2^L \end{pmatrix} \begin{pmatrix} L_1 \\ L_2 \end{pmatrix}$$

to obtain $$\begin{pmatrix} L_1^n \\ L_s^n \end{pmatrix} = D^{-1} \begin{pmatrix} \bar{\mu}_2^L & -\bar{\mu}_2^H \\ -\bar{\mu}_1^L & \bar{\mu}_1^H \end{pmatrix} \begin{pmatrix} g_H + g_H^{(BH)}(L_1^{n-1}, L_2^{n-1}) \\ g_L + g_L^{(BH)}(L_1^{n-1}, L_2^{n-1}) \end{pmatrix}.$$

After step 518, step 520 of process 450 inquiries whether the stopping criteria have been satisfied. In one implementation, the stopping criteria are satisfied when the values $L_1$ and $L_2$ satisfy a predetermined convergence criteria, such as whether the difference between each current and previous values of $L_1$ and $L_2$ are less than a predefined threshold. The stopping criteria can also be conditioned on whether a maximum number of iterations has been reached. If stopping criteria have not been satisfied, then the loop variable n is incremented at step 518 and the loop begins again starting from step 514.

Figure 6:
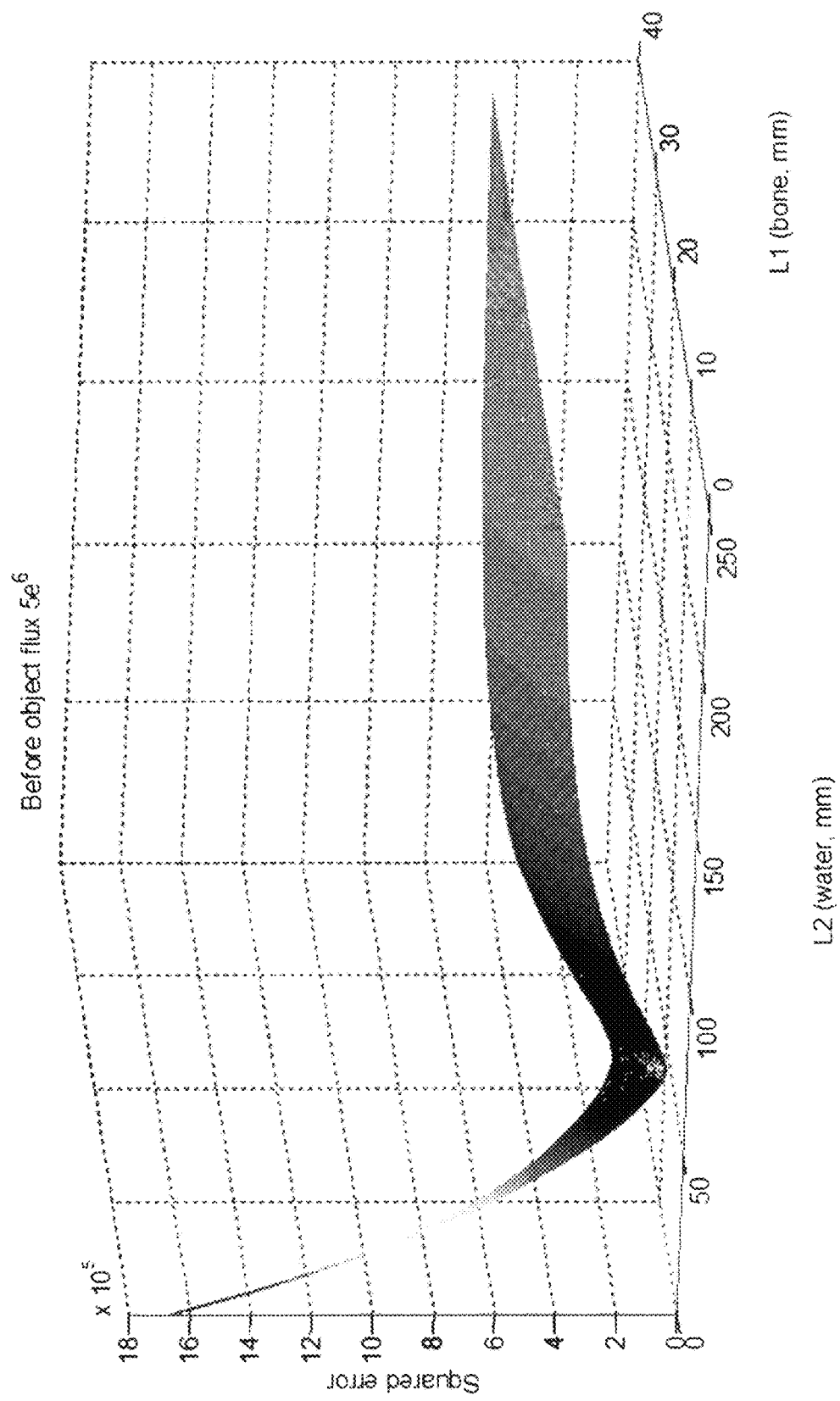
FIG. 6 shows a plot of a cost function for low X-ray flux.
Figure 7:
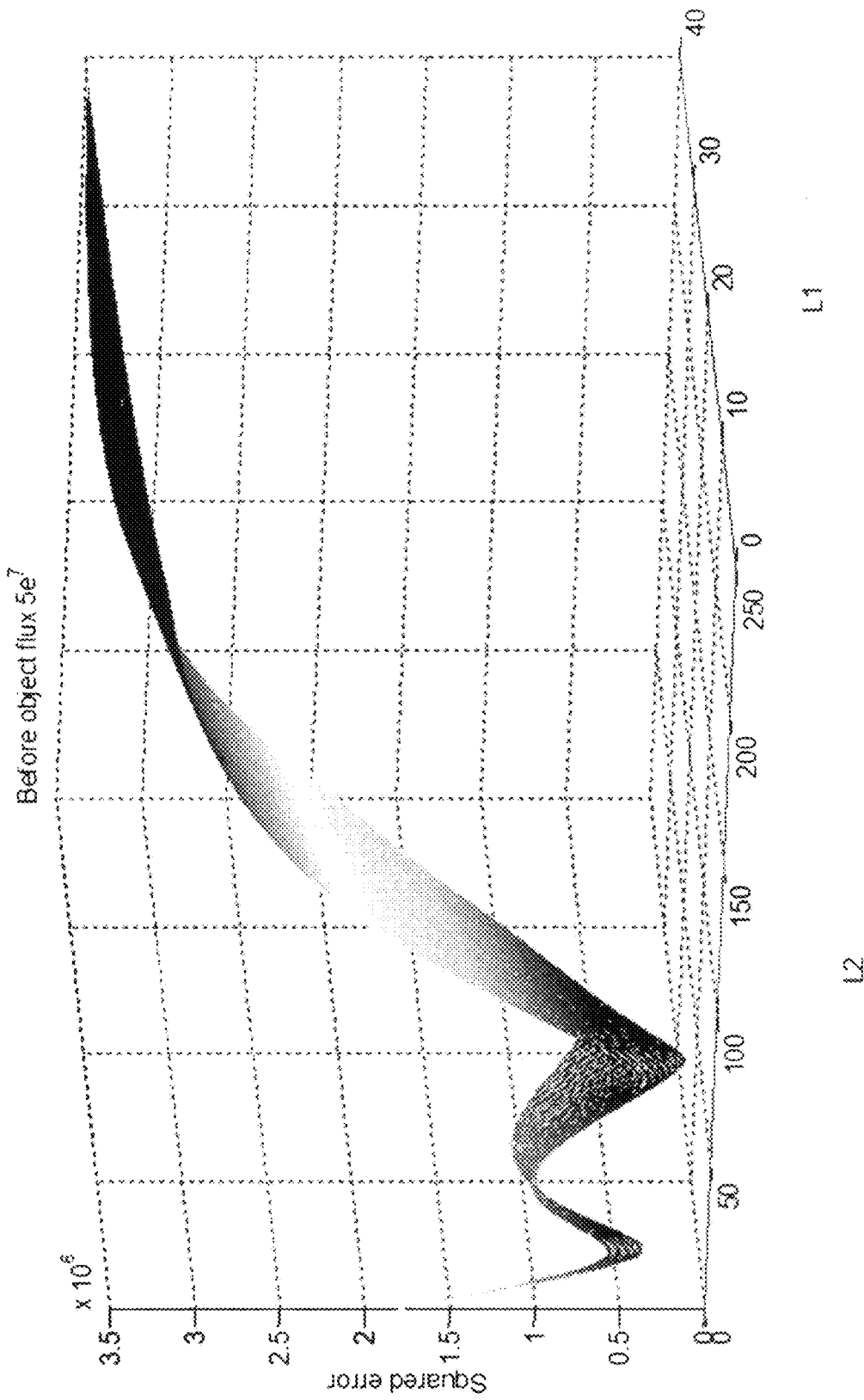
FIG. 7 shows a plot of a cost function for high X-ray flux.

In both method 200 and method 400 the efficiency, and often the result of the iterative search for the optimal projection lengths, depends on the initial estimates of the projection lengths. A well-chosen initial estimate can be obtained using an appropriate initial-estimate method. The initial-estimate method can also be tailored to the parameters of a CT scan being considered. For example, FIGS. 6 and 7 show the differences between a cost function calculated for high and low X-ray flux densities at the X-ray source. Depending on the X-ray flux density, it may be advantageous to bias the initial estimate of the projection lengths higher or lower. While the implementation shown in FIGS. 6 and 7 show water and bone as the two material components in the material decomposition, one of ordinary skill in the art will recognize that other material components can be used.

FIGS. 6 and 7 show respective plots of the least-square cost function plotted as a function of a first material and a second material. FIG. 6 shows the cost function for low-flux density at the X-ray source, and FIG. 7 shows the cost function for high-flux density. In both FIG. 6 and FIG. 7 the optimal projection length is $L_1=10$ mm and $L_2=40$ mm.

FIGS. 6 and 7 illustrate factors relevant to biasing the initial projection lengths estimate. When the flux incident on the PCDs is low, as in FIG. 6, the initial projections lengths should be biased lower in order that the search algorithm can take advantage of the steeper gradient of the cost function. In contrast, when the reference intensity $I_{ref}$ is high, as in FIG. 7, the initial projections lengths should be biased higher in order that the search algorithm can take advantage of the steeper gradient of the cost function and in order to avoid the purely local minimum visible at lower projection lengths.

The rational for biasing the initial estimate is especially compelling when a gradient-descent method is used to search for the optimal projection lengths. When, in method 400, a gradient-descent method is used to search for the optimal projection lengths, the rate of convergence depends on the gradient of the cost function. Therefore, for low incident flux density, as shown in FIG. 6, biasing the initial estimate lower can result in faster convergence.

In contrast, for high incident flux density, as shown in FIG. 7, the gradient is steeper when the initial estimate of the projection lengths is biased higher. Moreover, at high incident flux density, there is a purely local minimum of the cost function occurring at small projection lengths. By biasing the initial estimate of the projection lengths to be greater than the optimal projection lengths, this undesired local minimum can be avoided.

In summary, by choosing an initial projection-lengths estimate to correspond with a steeper gradient of the cost function, gradient-descent methods will converge more quickly. For low-flux densities the gradient of the cost function is generally steeper for estimates of the projection lengths that are collectively less than (i.e., biased lower than) the optimal projection lengths. On the other hand, for high-flux densities, the gradient of cost function is generally steeper for estimates of the projection lengths that are collectively greater than (i.e., biased greater than) the optimal projection lengths. Further, for high-flux densities, local minima different from the global minimum are more likely to be avoided by an initial projection-lengths estimate that is collectively greater than the optimal projection lengths.

Figure 8:
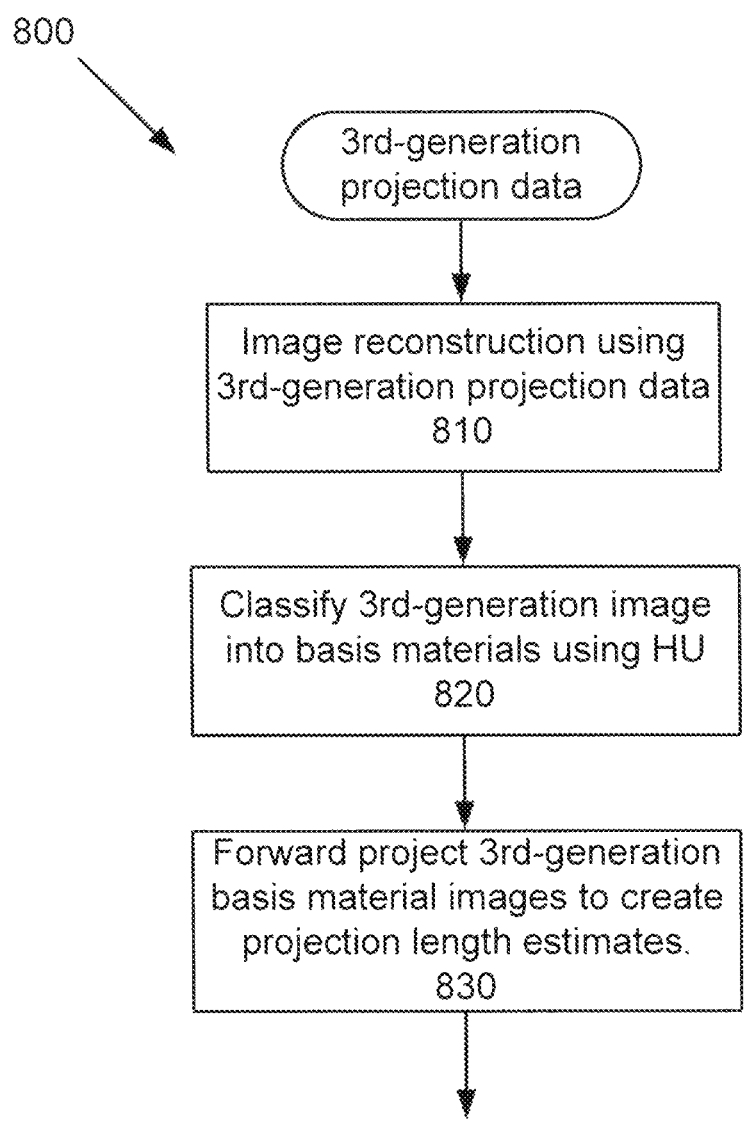
FIG. 8 shows a flow diagram of an implementation of an initial-estimate method for finding an initial estimation of the projection lengths.

FIG. 8 shows another method for obtaining the initial estimates of the projection lengths. This method decomposes a reconstructed image from non-spectral projection data into material components, and then forward projects the material component images to obtain an initial estimate of the projection lengths.

FIG. 8 shows a method 800 for deriving the projection-lengths estimate based on the Hounsfield units (HU) of a CT image reconstructed from non-spectral projection data. In one non-limiting exemplary implementation, the method relies on the assumption that, with a reconstructed image, the regions of very high attenuation correspond to bone, and regions of lower attenuation correspond to water. Also, a cross-over region being a mixture of water and bone is defined for an attenuation region that is between low and high.

The first step 810 in method 800 is to reconstruct an image using non-spectral projection data. The image reconstruction method can be a filtered back projection method, an iterative image reconstruction method, or a stochastic image reconstruction method. The image scale is given in HU by the function HU (x,y).

The non-limiting implementation shown in FIG. 8 shows that the projection data is from energy-integrating detectors arranged in a third-generation geometry. In one implementation, the reconstructed image can be derived from any non-spectral CT projection data. Additionally, in one implementation, non-spectral projection data can be derived from spectral CT projection data by summing the data over the spectral dimension for each detector and projection angle. After obtaining non-spectral data from the spectral data, an image can be reconstructed from this summed non-spectral projection data. In some cases, this spectral summing implementation might require initial preconditioning of the spectral projection data to correct for the nonlinear detector response of the PCDs.

Having reconstructed an attenuation image in step 810, method 800 proceeds to step 820, wherein regions of the reconstructed image are decomposed into material components of the first and second material, wherein the spatial function describing the concentrations of material 1 and material 2 are respectively given by $$c_1(x, y) = \begin{cases} \dfrac{HU(x, y) + 1000}{HU_1 + 1000} & HU(x, y) < HU_1 \\ \dfrac{HU(x, y) - HU_1}{HU_2 - HU_1} & HU_1 \leq HU(x, y) \leq HU_2, \text{ and} \\ 0 & HU(x, y) > HU_2 \end{cases}$$

$$c_2(x, y) = \begin{cases} 0 & HU(x, y) < HU_1 \\ \dfrac{HU(x, y) - HU_1}{HU_2 - HU_1} & HU_1 \leq HU(x, y). \end{cases}$$

The constants $HU_1$ and $HU_2$ are respectively thresholds representing a transition from being completely the first material to a mixed material, and from being a mixed material to being completely the second material.

Having separated the reconstructed image into material components in step 820, method 800 proceeds to step 830. In step 830 projection lengths are obtained by performing forward projections (e.g., Radon transforms—line integrals along the trajectories of the detected X-rays) on the spatial functions $c_1(x,y)$ and $c_2(x,y)$.

The image reconstruction problem, and also the forward projection problem, can be formulated as a matrix equation $$Af=g,$$

where g are the projection measurements of the X-rays transmitted through an object space that includes the object OBJ, A is the system matrix describing the discretized line integrals (i.e., the Radon transforms) of the X-rays through the object space, and f is the image of object OBJ (i.e., the quantity to be solved for by solving the system matrix equation). The image f is a map of the attenuation as a function of position. Thus, the projection estimates are given by $$Ac_1 = L_1 \text{ and } Ac_2 = L_2,$$

wherein $c_1$ and $c_1$ are respectively the column vector forms of the material concentrations $c_1(x,y)$ and $c_2(x,y)$.

The projection lengths output from step 830 can then be used as the initial estimate in either step S206 of method 200 or in step 410 of method 400.

Figure 9B:
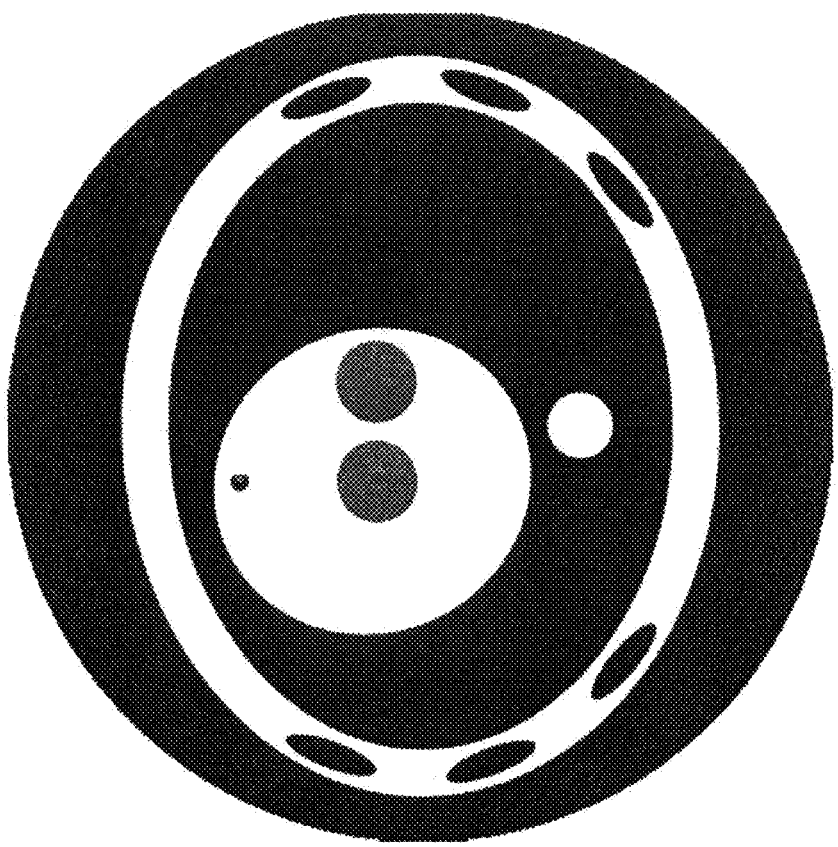
FIG. 9B shows a reconstructed image of the material decomposition for a material 1 using spectral CT data.
Figure 9A:
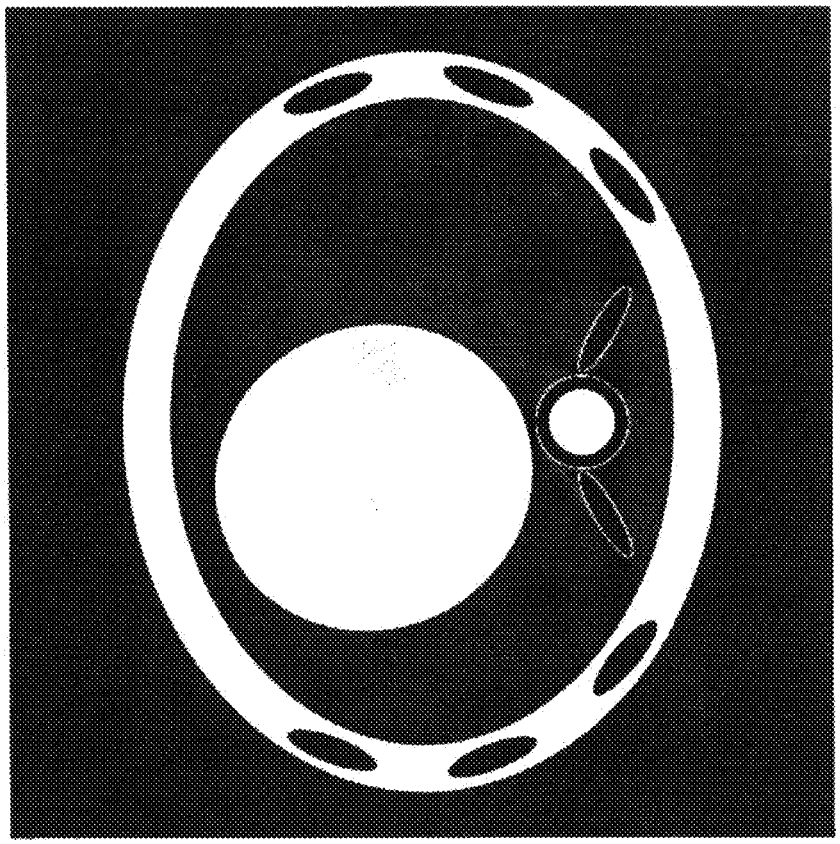
FIG. 9A shows a reconstructed image of the estimated material decomposition for a material 1 using non-spectral CT data from energy-integrating detectors, method 800 is used for the estimated material decomposition.

FIG. 9A and FIG. 9B show reconstructed images of a phantom. FIG. 9A shows an estimated image of the first material $c_1(x,y)$ using the projection data from energy-integrating detectors and the HU material decomposition equations in method 800. FIG. 9B shows a true-to-phantom reconstructed image of the first material using spectral projection data. As can be seen, the images in FIG. 9A and FIG. 9B mostly agree, with differences primarily manifesting in the transition/boundary regions.

Figure 10B:
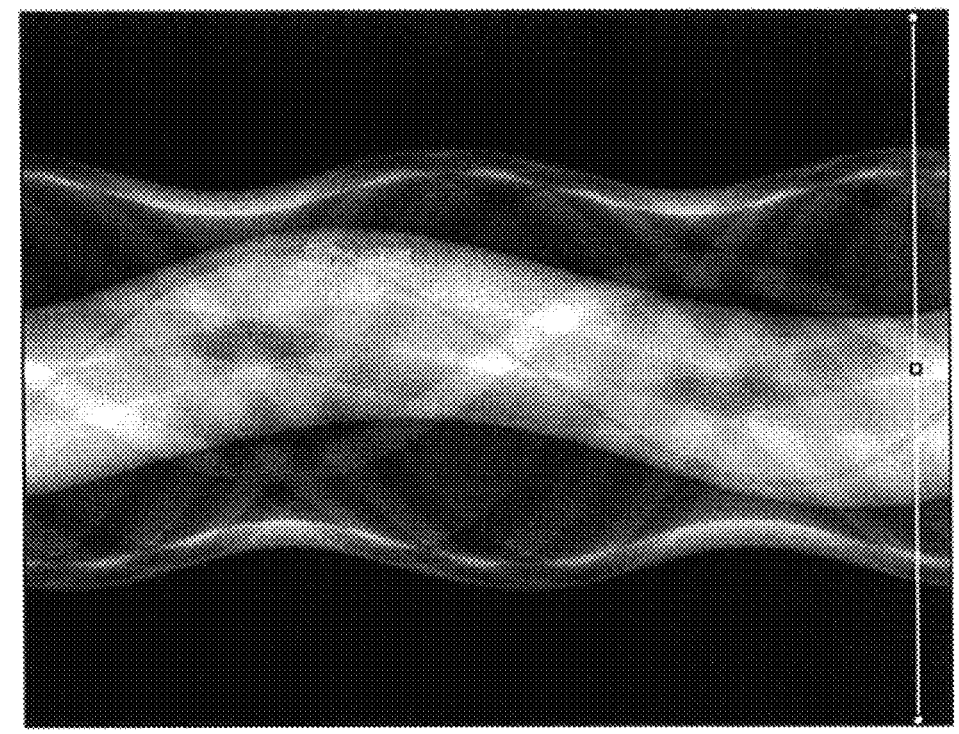
FIG. 10B shows a plot of a sinogram of the optimal projection lengths of material 1 from spectral CT data used in reconstructing the material 1 image shown in FIG. 9B.
Figure 10A:
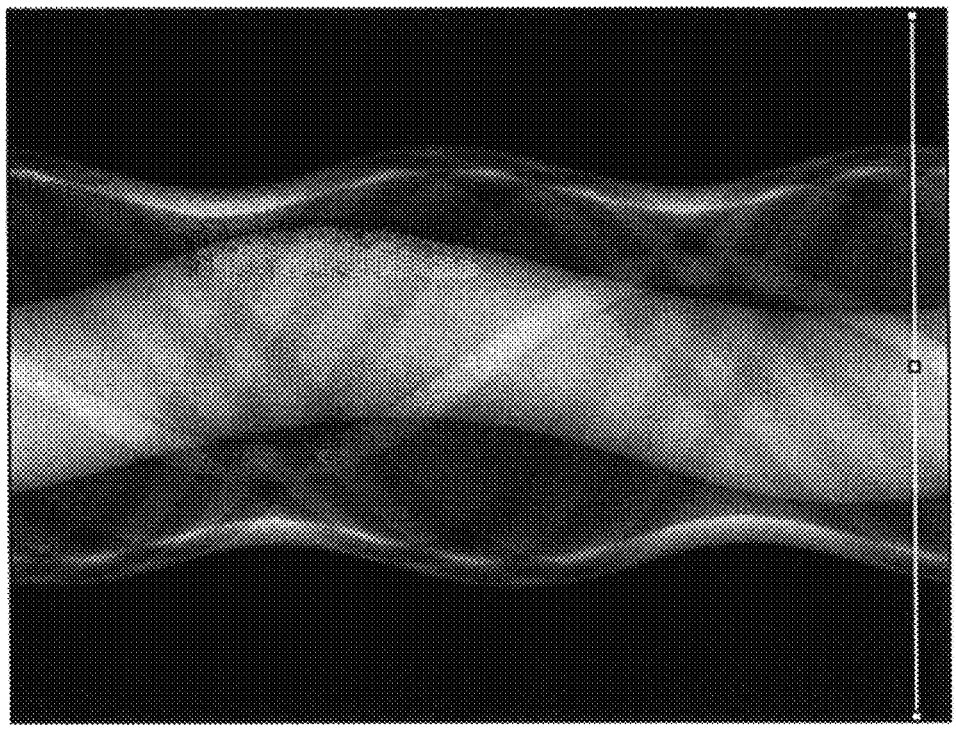
FIG. 10A shows a plot of a sinogram obtained from forward projections on the estimated material 1 reconstructed image shown in FIG. 9A.

FIG. 10A and FIG. 10B show sinograms corresponding respectively to FIG. 9A and FIG. 9B. FIG. 10A shows an estimated of the projection lengths of the first material $L_1$. FIG. 10B shows a sinogram of the projection lengths of the true phantom of the first material corresponding to the image shown in FIG. 9B. Consistent with the similarities between FIG. 9A and FIG. 9B, FIG. 10A shows strong similarities with FIG. 10B, demonstrating that method 800 provides a well-chosen initial estimate of the projection lengths. Also shown along the bottom of these two sinograms is a line corresponding to lineouts taken from the sinograms and shown in FIG. 11 for comparison.

Figure 11:
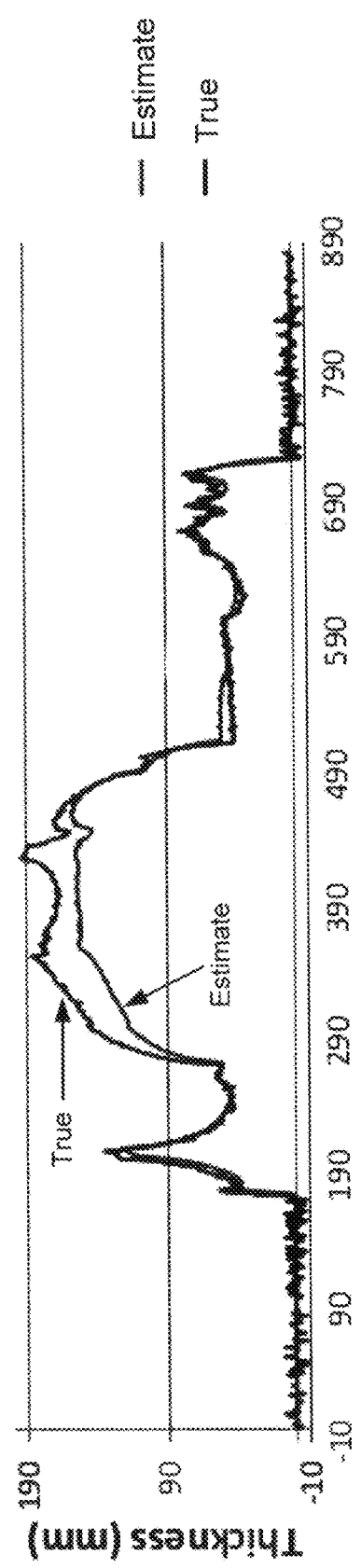
FIG. 11 shows a plot comparing a line-out of the sinogram in FIG. 10A (estimate) with a corresponding lineout of the sinogram in FIG. 10B (true)

FIG. 11 compares lineouts of the estimated and true projection lengths for the line shown on the sinogram in FIGS. 10A and 10B. FIG. 11 shows the projection-length values along the vertical axis and the pixel number along the horizontal axis. Again, strong correlations between the estimated and true projection lengths are visible in these plots, indicating that method 800 provides a good initial estimate for the iterative methods in FIGS. 2 and 4.

Figure 12B:
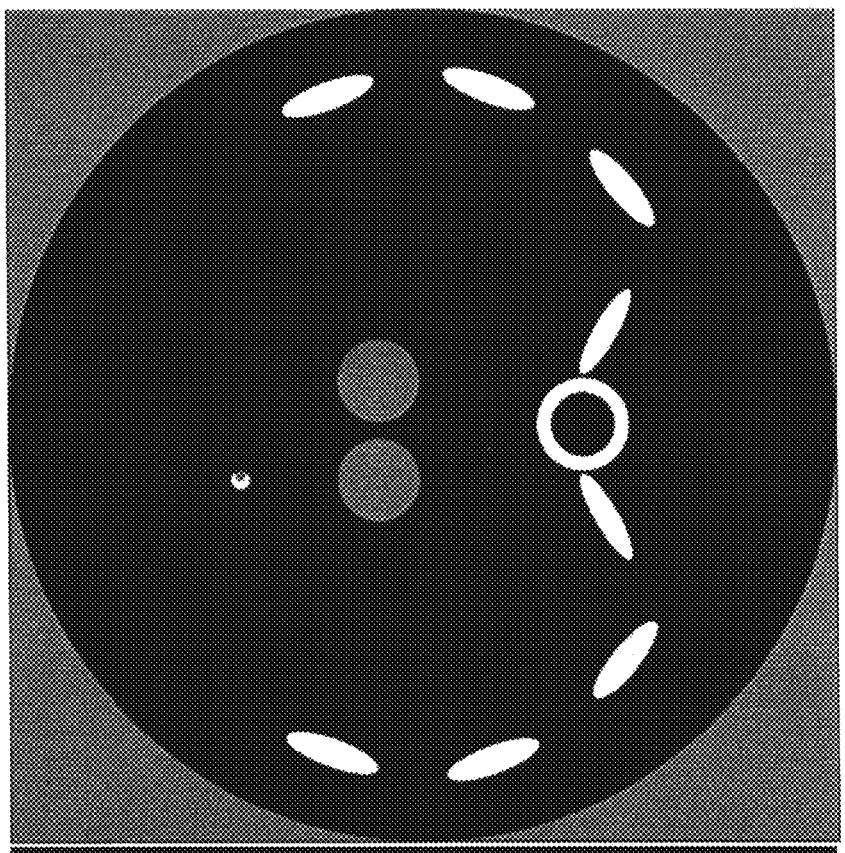
FIG. 12B shows a reconstructed image of the material decomposition for material 2 using spectral CT data.
Figure 12A:
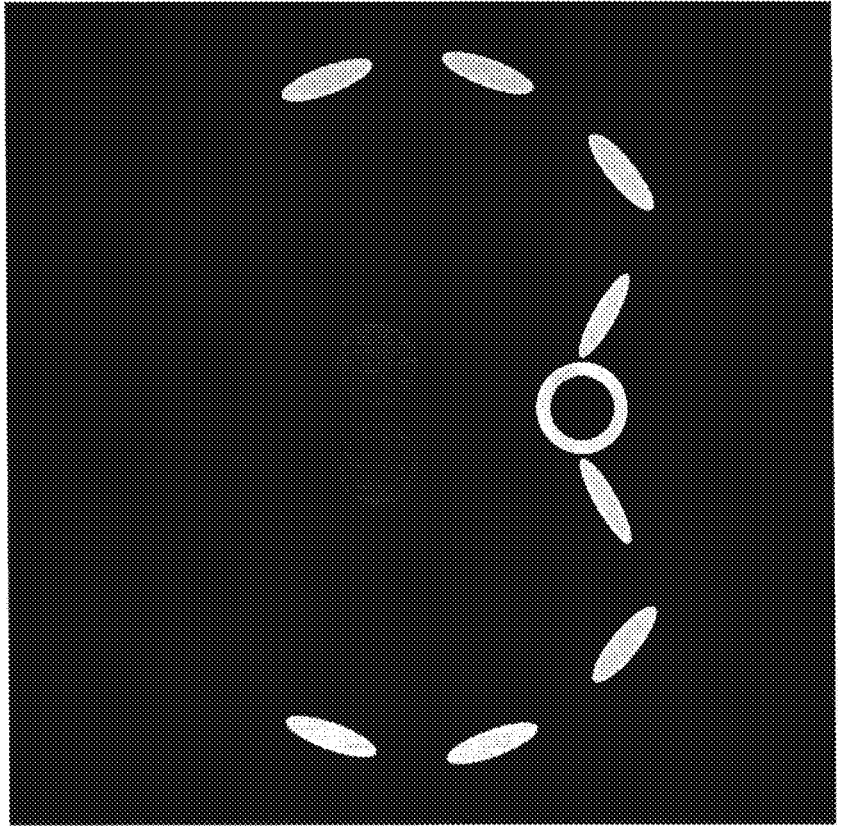
FIG. 12A shows a reconstructed image of the estimated material decomposition for material 2 using non-spectral CT data from energy-integrating detectors, method 800 is used for the estimated material decomposition.

FIG. 12A and FIG. 12B show reconstructed images of a phantom. FIG. 12A shows an estimated image of the second material $c_2(x,y)$ using the projection data from energy-integrating detectors and the HU material decomposition equations in method 800. FIG. 12B shows a true-to-phantom reconstructed image of the second material using spectral projection data. As can be seen, the images in FIG. 12A and FIG. 12B strongly agree.

Figure 13B:
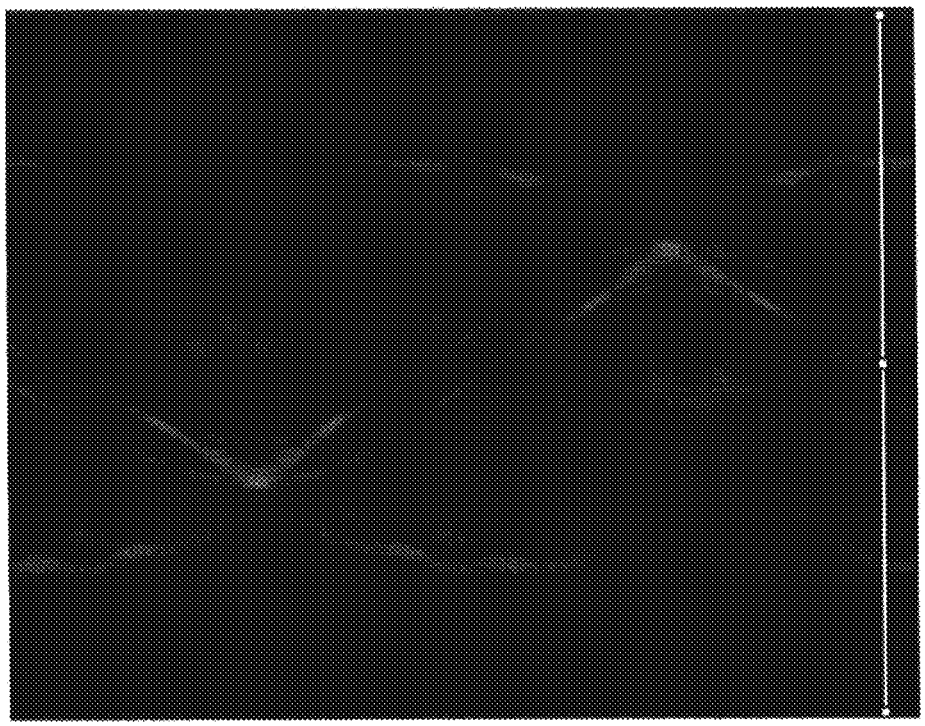
FIG. 13B shows a plot of a sinogram of the optimal projection lengths of material 2 from spectral CT data used in reconstructing the material 2 image shown in FIG. 12B.
Figure 13A:
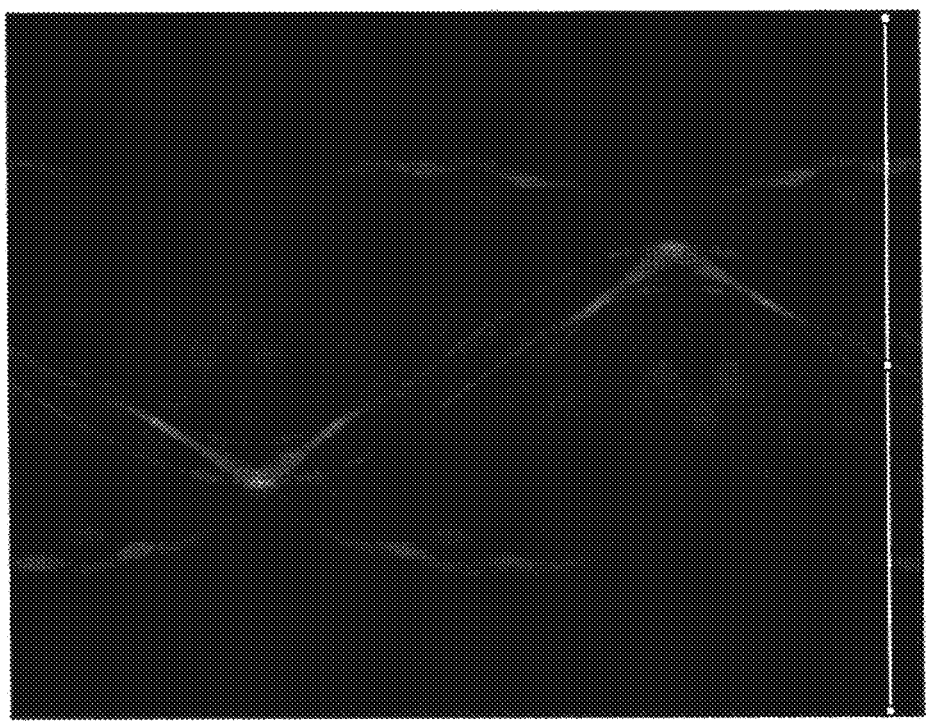
FIG. 13A shows a plot of a sinogram obtained from forward projections on the estimated material 2 reconstructed image shown in FIG. 12A.

FIG. 13A and FIG. 13B show sinograms corresponding respectively to FIG. 12A and FIG. 12B. FIG. 13A shows an estimate of the projection lengths of the second material $L_2$. FIG. 13B shows a sinogram of the projection lengths of the true phantom of the second material corresponding to the image shown in FIG. 12B. Consistent with the similarities between FIG. 12A and FIG. 12B, FIG. 13A shows strong similarities with FIG. 13B, demonstrating that method 800 provides a well-chosen initial estimate of the projection lengths. Also shown along the bottom of these two sinograms is a line corresponding to lineouts taken from the sinograms and shown in FIG. 14 for comparison.

Figure 14:
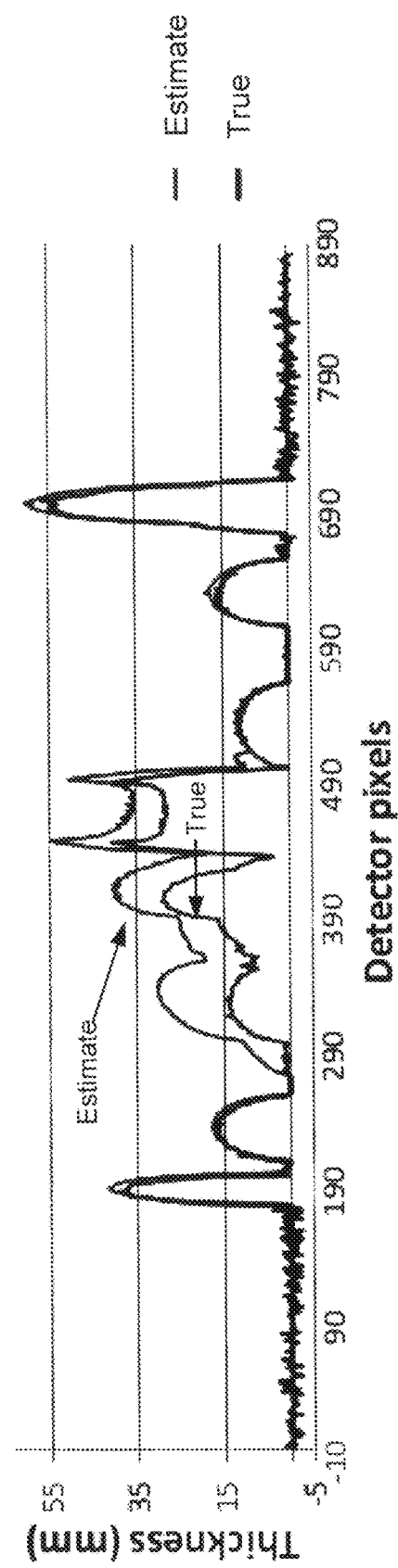
FIG. 14 shows a plot comparing a line-out of the sinogram in FIG. 13A (estimate) with a corresponding lineout of the sinogram in FIG. 13B (true)

FIG. 14 compares lineouts of the estimated and true projection lengths for the line shown on the sinogram in FIGS. 13A and 13B. FIG. 14 shows the projection-length values along the vertical axis and the pixel number along the horizontal axis. Again, strong correlations between the estimated and true projection lengths are visible in these plots, indicating that method 800 provides a good initial estimate for the iterative methods in FIGS. 2 and 4.

Figure 15:
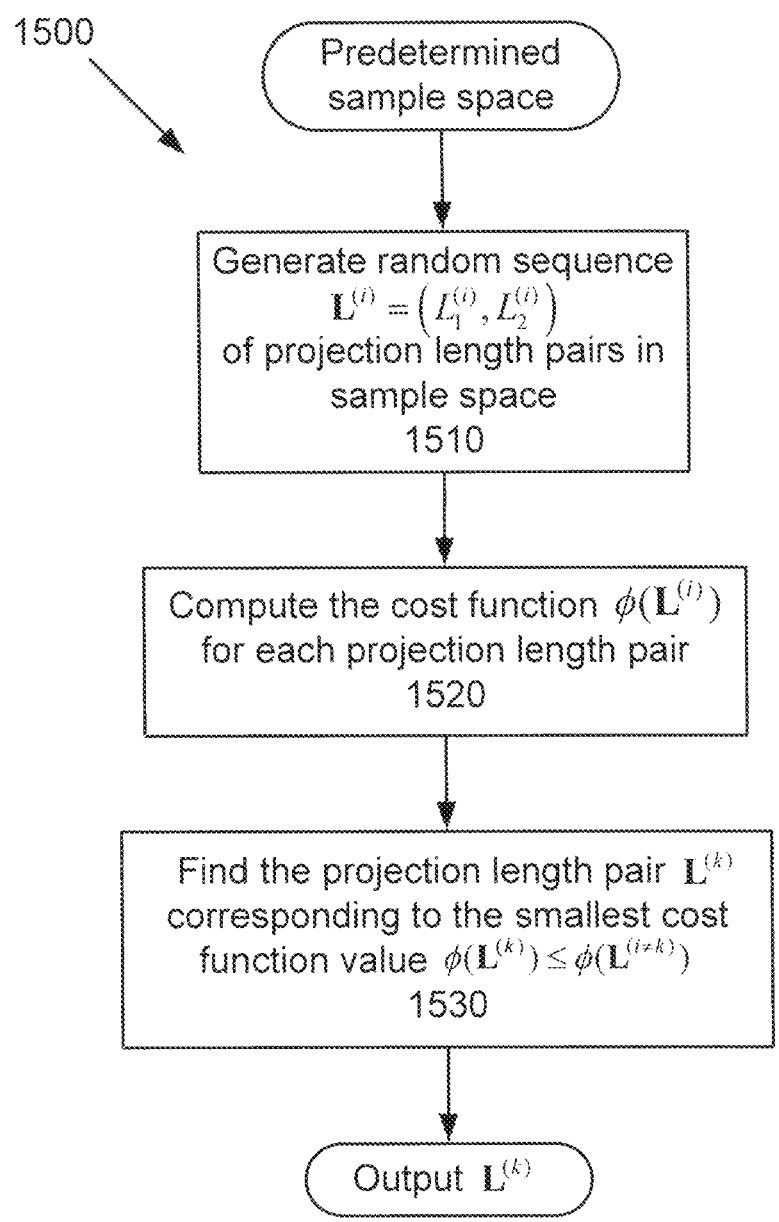
FIG. 15 shows a flow diagram of an implementation of a random sampling method to obtain/refine an estimate of the material-decomposition projection lengths.

FIG. 15 shows a method 1500 of obtaining an initial estimate of the projection lengths. This method 1500 begins by receiving a predetermined sample space. For example, the predetermined sample space can be given as collection of projection lengths within a predetermined distance of the initial estimate obtained using method 400. Alternatively, the predetermined sample space can be obtained by some other method. For example, the sample space could include the collection of all combination of projection lengths resulting in the detected absorption.

In step 1510 of method 1500, a random collection of projection length pairs are selected at random from the predetermined sample space.

Next, in step 1520, the cost function $\varphi(L^{(i)})$ is calculated for each projection length pair $L^{(i)}$ in the collection of projection length pairs.

Next, in step 1530, the projection lengths corresponding to the cost function with the lowest value is selected as the projection lengths estimate. And this projection lengths estimate is the output of the method 1500.

The method 1500 can be used by itself to obtain an initial estimate of the projection lengths, or method 1500 can be used together with either the biasing method or with method 800, or method 1500 can be used together with both the biasing method and with method 800. For example, in one implementation, method 800 could be used to obtain a first initial estimate, and the first initial estimate can be used to define a predetermined sample space for method 1500. Then method 1500 can use the predetermined sample space from method 800 to obtain a second initial estimate. Then, the second initial estimate can be biased higher or lower according to the biasing method to obtain a third initial estimate. Any of these three initial estimates or even a weighted average of the three initial estimates can be used as the initial estimate in the iterative method to obtain the optimized projection lengths. Alternatively, the first initial estimate obtained using method 800 can be biased higher or lower according to the biasing method to obtain a fourth initial estimate. One of ordinary skill in the art will recognize that there are many combinations and sub-combinations of these initial estimate methods that will provide an initial estimate.

While certain implementations have been described, these implementations have been presented by way of example only, and are not intended to limit the teachings of this disclosure. Indeed, the novel methods, apparatuses and systems described herein may be embodied in a variety of other forms; furthermore, various omissions, substitutions and changes in the form of the methods, apparatuses and systems described herein may be made without departing from the spirit of this disclosure.

The invention claimed is:

1. An apparatus to process projection measurements, the apparatus comprising:
processing circuitry configured to
obtain projection data representing an irradiance of radiation detected at a plurality of detectors, the radiation having been transmitted through an object space, wherein the projection data includes a spectral dataset having a plurality of energy components, and each energy component corresponds to a sub-band of a total energy band of the radiation;
calculate model data representing calculations of the irradiance of the radiation transmitted through the object space, the calculations of the irradiance being performed using a detector model that approximates a detector response and that approximates attenuation of the radiation using a plurality of projection lengths using a plurality of material models, wherein the detector response represents a relation between measured values of the projection data and the irradiance of the radiation on the plurality of detectors;
calculate a cost function representing a difference between the obtained projection data and the calculated model data;
choose, using an initial-estimate method, initial projection lengths; and
optimize, using an iterative-optimization method, the plurality of projection lengths by updating the plurality of projection lengths to minimize the cost function, the iterative-optimization method starting the updating of the plurality of projection lengths using the initial projection lengths, wherein
the initial projection lengths are chosen by the initial-estimate method to improve performance of the iterative-optimization method by one or more of (i) decreasing a time to converge to a plurality of projection lengths that minimizes the cost function and (ii) increasing a likelihood of converging to a plurality of projection lengths that are a global minimum of the cost function.

2. The apparatus according to claim 1, wherein the processing circuitry is further configured to
obtain the projection data, which includes a non-spectral dataset, wherein the plurality of detectors includes energy-integrating detectors and the non-spectral dataset represents the irradiance of radiation detected at the energy-integrating detectors.

3. The apparatus according to claim 2, wherein the processing circuitry is further configured to
optimize the plurality of projection lengths, wherein the initial-estimate method is a density-based initial-estimate method determining a first initial projection length and a second initial projection length respectively corresponding to a first material and a second material by
reconstructing an attenuation image using the non-spectral dataset,
mapping the attenuation image onto respective first and second material components,
performing a forward projection on the first material component to obtain the first initial projection length, and
performing the forward projection on the second material component to obtain the second initial projection length.

4. The apparatus according to claim 3, wherein the processing circuitry is further configured to
optimize the plurality of projection lengths by mapping the attenuation image onto the respective first and second material components, wherein, for respective points in the attenuation image,
an attenuation of the first material component is set to the attenuation of the attenuation image, and an attenuation of the second material component is set to zero, when the attenuation of the attenuation image is less than a first predefined attenuation value,
the attenuation of the first material component is zero, and the attenuation of the second material component is set to the attenuation of the attenuation image, when the attenuation of the attenuation image is greater than a second predefined attenuation value, which is great than the first predefined attenuation value, and
the respective attenuations of the first and second material components each being set greater than zero that sum to the attenuation of the attenuation image, when the attenuation of the attenuation image is between the first and second predefined attenuation values.

5. The apparatus according to claim 1, wherein the processing circuitry is further configured to
optimize the plurality of projection lengths, wherein the initial-estimate method to determine the initial projection lengths includes a random search, wherein the random search includes
randomly selecting a plurality of sample points corresponding to the projection lengths within a search region,
calculating cost-function values for the plurality of sample points, and
selecting the initial projection lengths to be the sample point of the plurality of sample points corresponding to the smallest calculated cost-function value.

6. The apparatus according to claim 5, wherein the processing circuitry is further configured to
optimize the plurality of projection lengths, wherein a center of the search region is given by a first initial projection length and a second initial projection length corresponding respectively to a first material and a second material, and the first and the second initial projection lengths are obtained using a density-based initial-estimate that includes
reconstructing an attenuation image using a non-spectral dataset of the projection data,
mapping the attenuation image onto respective first and second material components,
performing a forward projection on the first material component to obtain the first initial projection length, and
performing the forward projection on the second material component to obtain the second initial projection length.

7. The apparatus according to claim 6, wherein the processing circuitry is further configured to optimize the plurality of projection lengths using a Radon transform as the forward projection on the respective first and second material components.

8. The apparatus according to claim 1, wherein the processing circuitry is further configured to
optimize the plurality of projection lengths according to a biasing method, wherein the initial projection lengths are biased according to a predetermined amount relative to a first estimate of the projection lengths and an amount of the bias is conditioned on an irradiance of radiation incident on the object space.

9. The apparatus according to claim 8, wherein the processing circuitry is further configured to
optimize the plurality of projection lengths according to the biasing method, wherein
each of the initial projection lengths is set greater than the corresponding projection length of the first estimate of the projection lengths when the irradiance of the radiation incident on the object space is greater than a predetermined first irradiance threshold,
each of the initial projection lengths is set less than the corresponding projection length of the first estimate of the projection lengths when the irradiance of the radiation incident on the object space is less than a predetermined second irradiance threshold, and
the initial projection lengths are set to the first estimate of the projection lengths when the incident irradiance on the object space is between the predetermined second irradiance threshold and the first irradiance threshold.

10. The apparatus according to claim 9, wherein the processing circuitry is further configured to
optimize the plurality of projection lengths according to the biasing method, wherein the first estimate of the projection lengths is given by a first initial projection length and a second initial projection length corresponding respectively to a first material and a second material, and the first and the second initial projection lengths are obtained using a density-based initial-estimate that includes
reconstructing an attenuation image using a non-spectral dataset of the projection data,
mapping the attenuation image onto respective first and second material components,
performing a forward projection on the first material component to obtain the first initial projection length, and
performing the forward projection on the second material component to obtain the second initial projection length.

11. The apparatus according to claim 1, wherein the processing circuitry is further configured to
obtain a non-spectral dataset by summing the respective energy components of the spectral dataset, and
optimize the plurality of projection lengths, wherein the initial-estimate method is a density-based initial-estimate method determining a first initial projection length and a second initial projection length respectively corresponding to a first material and a second material by
reconstructing an attenuation image using the non-spectral dataset,
mapping the attenuation image onto respective first and second material components,
performing a forward projection on the first material component to obtain the first initial projection length, and
performing the forward projection on the second material component to obtain the second initial projection length.

12. A photon-counting computed tomography apparatus, comprising:
a radiation source radiating radiation into an object space;
a plurality of detector elements configured to detect radiation transmitted from the radiation source and through the object space, the plurality of detector elements configured to generate projection data representing an irradiance of the radiation at the plurality of detectors, wherein the plurality of detector elements including a plurality of photon-counting detectors each configured to detect a plurality of energy components of the radiation, and each energy component corresponds to a sub-band of a total energy band of the radiation;
a rotation mount configured to rotate the X-ray source around the object space, wherein the X-ray source is fixedly connected to the rotation mount; and
processing circuitry configured to
obtain projection data representing the irradiance of the radiation detected at the plurality of detectors, the radiation having been transmitted through the object space, wherein the projection data includes a spectral dataset representing the detection by the photon-counting detectors having the plurality of energy components;
calculate model data representing calculations of the irradiance of the radiation transmitted through the object space, the calculations of the irradiance being performed using a detector model that approximates a detector response and that approximates attenuation of the radiation using a plurality of projection lengths using a plurality of material models, wherein the detector response represents a relation between measured values of the projection data and the irradiance of the radiation on the plurality of detectors;
calculate a cost function representing a difference between the obtained projection data and the calculated model data;
choose, using an initial-estimate method, initial projection lengths; and
optimize, using an iterative-optimization method, the plurality of projection lengths by updating the plurality of projection lengths to minimize the cost function, the iterative-optimization method starting the updating of the plurality of projection lengths using the initial projection lengths, wherein
the initial projection lengths are chosen by the initial-estimate method to improve performance of the iterative-optimization method by one or more of (i) decreasing a time to converge to a plurality of projection lengths that minimizes the cost function and (ii) increasing a likelihood of converging to a plurality of projection lengths that are a global minimum of the cost function.

13. An imaging method, comprising:
obtaining projection data representing an irradiance of radiation detected at a plurality of detectors, the radiation having been transmitted through an object space, wherein the projection data includes a spectral dataset having a plurality of energy components, and each energy component corresponds to a sub-band of a total energy band of the radiation;

calculating model data representing calculations of the irradiance of the radiation transmitted through the object space, the calculations of the irradiance being performed using a detector model that approximates a detector response and that approximates attenuation of the radiation using a plurality of projection lengths using a plurality of material models, wherein the detector response represents a relation between measured values of the projection data and the irradiance of the radiation on the plurality of detectors;

calculating a cost function representing a difference between the obtained projection data and the calculated model data;

choosing, using an initial-estimate method, initial projection lengths; and optimizing, using an iterative-optimization method, the plurality of projection lengths by updating the plurality of projection lengths to minimize the cost function, the iterative-optimization method starting the updating of the plurality of projection lengths using the initial projection lengths, wherein the initial projection lengths are chosen by the initial-estimate method to improve performance of the iterative-optimization method by one or more of (i) decreasing a time to converge to a plurality of projection lengths that minimizes the cost function and (ii) increasing a likelihood of converging to a plurality of projection lengths that are a global minimum of the cost function.

14. The method according to claim 13, wherein the projection data includes a non-spectral dataset representing the irradiance of radiation detected at energy-integrating detectors, and the plurality of detectors includes energy-integrating detectors.

15. The method according to claim 14, wherein the step of optimizing the plurality of projection lengths further includes the initial-estimate method being a density-based initial-estimate method determining a first initial projection length and a second initial projection length respectively corresponding to a first material and a second material by reconstructing an attenuation image using the non-spectral dataset, mapping the attenuation image onto respective first and second material components, performing a forward projection on the first material component to obtain the first initial projection length, and performing the forward projection on the second material component to obtain the second initial projection length.

16. The method according to claim 15, wherein the step of optimizing the plurality of projection lengths further includes the step of mapping the attenuation image, in the density-based initial-estimate method, being performed by mapping the attenuation image onto the respective first and second material components according to, for respective points in the attenuation image, an attenuation of the first material component is set to the attenuation of the attenuation image, and an attenuation of the second material component is zero, when the attenuation of the attenuation image is less than a first predefined attenuation value, the attenuation of the first material component is zero, and the attenuation of the second material component is set to the attenuation of the attenuation image, when the attenuation of the attenuation image is greater than a second, predefined attenuation value, which is great than the first predefined attenuation value, and the respective attenuations of the first and second material components each being set greater than zero that sum to the attenuation of the attenuation image, when the attenuation of the attenuation image is between the first and second predefined attenuation values.

17. The method according to claim 13, wherein the step of optimizing the plurality of projection lengths further includes the initial-estimate method to determine the initial projection lengths including a random search performed by randomly selecting a plurality of sample points corresponding to the projection lengths within a search region, calculating cost-function values for the plurality of sample points, and selecting the initial projection lengths to be the sample point of the plurality of sample points corresponding to the smallest calculated cost-function value.

18. The method according to claim 13, wherein the step of optimizing the plurality of projection lengths further includes the initial-estimate method determining the initial projection lengths using a biasing method, wherein the initial projection lengths are conditionally biased on an irradiance of radiation incident on the object space wherein each of the initial projection lengths is set greater than the corresponding projection length of the first estimate of the projection lengths when the irradiance of the radiation incident on the object space is greater than a predetermined first irradiance threshold, each of the initial projection lengths is set less than the corresponding projection length of the first estimate of the projection lengths when the irradiance of the radiation incident on the object space is less than a predetermined second irradiance threshold, and the initial projection lengths are set to the first estimate of the projection lengths when the irradiance of the radiation incident object space is between the predetermined second irradiance threshold and the first irradiance threshold.

19. A non-transitory computer-readable medium storing executable instructions, wherein the instructions, when executed by processing circuitry, cause the processing circuitry to perform the method according to claim 13.

* * * * *